US010098216B2

United States Patent
Kabumoto et al.

(10) Patent No.: US 10,098,216 B2
(45) Date of Patent: Oct. 9, 2018

(54) X-RAY GENERATOR AND X-RAY INSPECTION APPARATUS

(71) Applicants: ISHIDA CO., LTD., Kyoto-shi, Kyoto (JP); JOB CORPORATION, Yokohama-shi, Kanagawa (JP)

(72) Inventors: Takashi Kabumoto, Ritto (JP); Keiichiro Yamamoto, Yokohama (JP); Atsushi Iwai, Ritto (JP)

(73) Assignees: ISHIDA CO., LTD., Kyoto (JP); JOB CORPORATION, Kanagawa (JP)

(*) Notice: Subject to any disclaimer, the term of this patent is extended or adjusted under 35 U.S.C. 154(b) by 0 days.

(21) Appl. No.: 15/753,146

(22) PCT Filed: Aug. 4, 2016

(86) PCT No.: PCT/JP2016/072965
§ 371 (c)(1),
(2) Date: Feb. 15, 2018

(87) PCT Pub. No.: WO2017/030003
PCT Pub. Date: Feb. 23, 2017

(65) Prior Publication Data
US 2018/0242440 A1    Aug. 23, 2018

(30) Foreign Application Priority Data
Aug. 19, 2015 (JP) .................................. 2015-161894

(51) Int. Cl.
*G01N 23/04* (2018.01)
*H05G 1/54* (2006.01)
(Continued)

(52) U.S. Cl.
CPC ............... *H05G 1/26* (2013.01); *G01N 23/04* (2013.01); *H05G 1/06* (2013.01); *H05G 1/025* (2013.01)

(58) Field of Classification Search
CPC . G06F 2203/04112; G06F 3/044; H05G 1/06; H05G 1/26; H05G 1/54; H05G 1/04;
(Continued)

(56) References Cited

U.S. PATENT DOCUMENTS 4,520,495 A    5/1985  Tanaka
5,398,274 A *  3/1995  Komatani .............. H05G 1/265
                                                        378/110
(Continued)

FOREIGN PATENT DOCUMENTS

JP    56-036900 A    4/1981
JP    58-094800 A    6/1983
(Continued)

OTHER PUBLICATIONS

Translation of the Written Opinion of the International Searching Authority, dated Feb. 20, 2018.

*Primary Examiner* — Irakli Kiknadze

(57) ABSTRACT

An inspection sorting apparatus includes an X-ray tube with an anode electrode and a cathode electrode, a tank housing the X-ray tube and having insulation oil contained therein, and the anode electrode and the cathode electrode are supplied with a predetermined voltage to generate X-ray. An inspection sorting apparatus has an abnormal discharge determination unit, an LCD display, and a notification control unit. The abnormal discharge determination unit individually detects a first abnormal discharge which is an abnormal discharge inside the X-ray tube, and a second abnormal discharge which is an abnormal discharge inside the tank outside the X-ray tube. The LCD display outputs notification information prompting an administrator to replace the X-ray tube or the tank. The notification control unit causes the LCD display to output the notification information in accordance with a detection result from the abnormal discharge determining unit.

8 Claims, 12 Drawing Sheets

(51) Int. Cl.
*H05G 1/26* (2006.01)
*H05G 1/06* (2006.01)
*H05G 1/02* (2006.01)

(58) Field of Classification Search
CPC .. H05G 1/08; H05G 1/10; H05G 1/12; H05G 1/22; H05G 1/265; H05G 1/30; H05G 1/32; H05G 1/34; H05G 1/46; H05G 1/56; C23C 26/00; C23C 26/02; C23C 30/00; A61B 10/0045; A61B 17/42; A61B 17/425; A61B 1/00016; A61B 1/00034; A61B 1/00096; A61B 1/00135; A61B 1/00142; A61B 1/00177; A61B 1/042; A61B 1/05; A61B 1/303; A61B 6/03; A61B 6/032; A61B 6/40; A61B 6/4435; A61B 6/54; A61B 6/542; A61B 6/508; G01N 2223/304; G01N 2223/419; G01N 23/046; G06T 11/003; G06T 2207/10072; G06T 2207/10116; H01J 2235/0233; H01J 35/025
USPC ................................. 378/62, 101, 109–117
See application file for complete search history.

(56) References Cited

U.S. PATENT DOCUMENTS

| | | | |
|---|---|---|---|
| 6,426,997 B1 * | 7/2002 | Fuchs | H01J 35/025 378/117 |
| 2001/0031036 A1 * | 10/2001 | Berezowitz | H05G 1/26 378/118 |
| 2002/0110219 A1 | 8/2002 | Yagi | |
| 2003/0076920 A1 * | 4/2003 | Shinno | A61B 6/032 378/4 |
| 2006/0008053 A1 * | 1/2006 | Ishikawa | H05G 1/30 378/111 |
| 2015/0199813 A1 * | 7/2015 | Yamahana | A61B 6/5258 378/8 |

FOREIGN PATENT DOCUMENTS

| | | |
|---|---|---|
| JP | 05-089995 A | 4/1993 |
| JP | 2001-145625 A | 5/2001 |
| JP | 2002-198199 A | 7/2002 |
| JP | 2010-033822 A | 2/2010 |

* cited by examiner

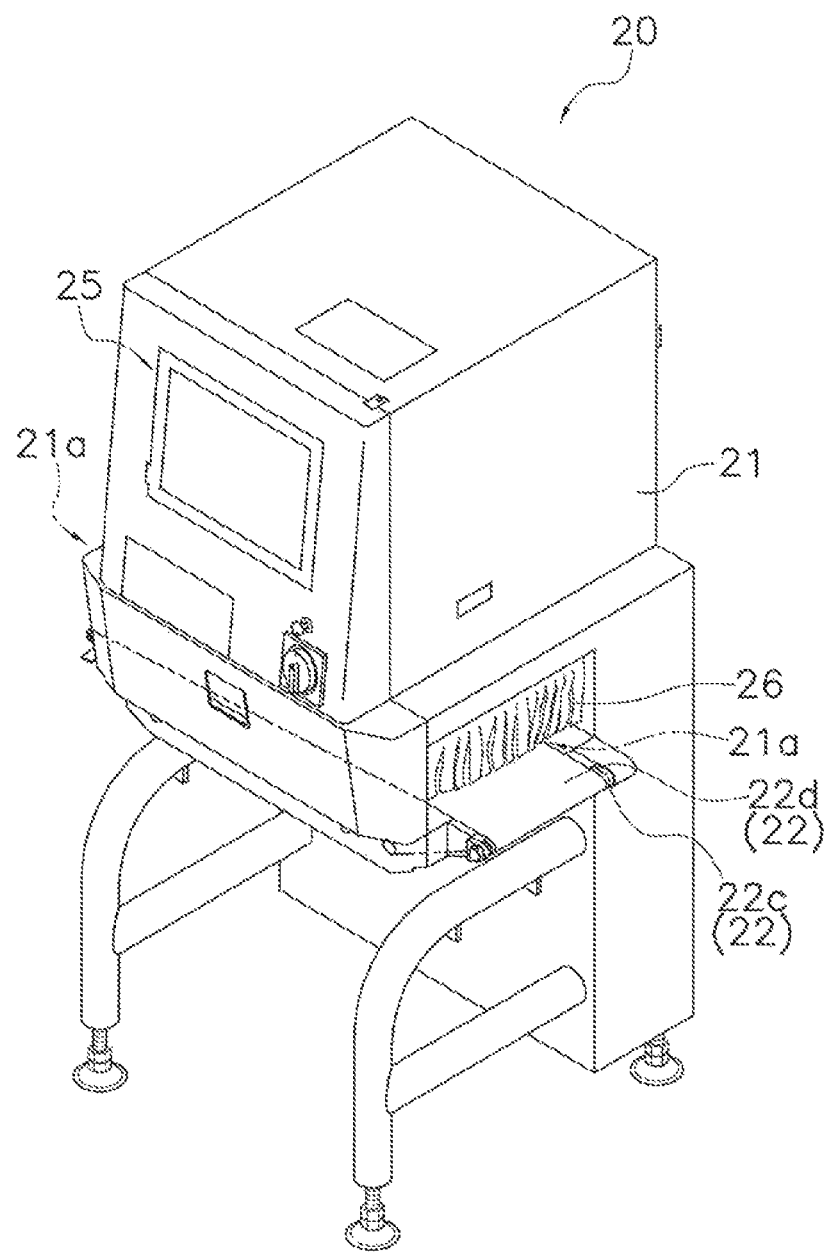
F I G. 2

X-RAY GENERATOR AND X-RAY INSPECTION APPARATUS

CROSS-REFERENCE TO RELATED APPLICATIONS

This U.S. National stage application claims priority under 35 U.S.C. § 119(a) to Japanese Patent Application No. 2015-161894, filed in Japan on Aug. 19, 2015, the entire contents of which are hereby incorporated herein by reference.

TECHNICAL FIELD

The present invention relates to an X-ray generator and an X-ray inspection apparatus.

BACKGROUND ART

Conventionally, an X-ray generator used for X-ray inspection performed by irradiating X-rays to an object to be inspected has an X-ray tube to an anode electrode and a cathode electrode, and a tank for housing the X-ray tube and having insulation oil contained therein. In the X-ray generator, by supplying a predetermined voltage to the anode electrode and the cathode electrode, electrons are emitted from the cathode electrode whereby the emitted electrons collide with the anode electrode to generate X-rays.

In such an X-ray generator, abnormal discharge (discharge which can be an obstacle to inspection) may occur in the X-ray tube or in the tank. Such abnormal discharge includes abnormal discharge caused by the lapse of service life and abnormal discharge, caused by the structure of the X-ray tube. The abnormal discharge caused by the lapse of service life can occur inside the X-ray tube or inside the tank outside the X-ray tube due to deterioration of vacuum degree and deterioration of insulation performance such as insulation oil. The abnormal discharge caused by the structure of the X-ray tube occurs inside the X-ray tube due to the fact that the electrons emitted from the cathode electrode stay in the X-ray tube without colliding with the anode electrode or the like, and has little relevance to the lapse of service life.

When abnormal discharge caused by the lapse of useful life occurs, using the apparatus in such a state will lead to a decline in the inspection accuracy. Therefore, it is desirable to inform the administrator for prompting him to perform maintenance such as replacing the X-ray tube. For example, Japanese Patent Application Laid-Open No. 2001-145625 discloses a technique in which when abnormal discharge in the X-ray tube occurs for a predetermined number of times or more within a fixed period, operation of the apparatus is terminated and a predetermined message is displayed on a display.

SUMMARY OF THE INVENTION

Technical Problem

In Patent Document 1, it is assumed that notification is given to the administrator when abnormal discharge occurs in the X-ray tube, but detection and notification are not particularly taken into consideration when abnormal discharge occurs inside the tank outside the X-ray tube. For this reason, when there is no occurrence of abnormal discharge inside the X-ray tube even when abnormal discharge occurs inside the tank outside the X-ray tube (that is, abnormal discharge due to the lapse of service life), the administrator is not notified of this. Therefore, even when the X-ray tube or the like reaches its replacement time, it can be assumed that notification to the administrator is not performed accurately. In this case, reliability is poor because the accuracy of inspection decreases.

Therefore, the object of the present invention is to provide an X-ray generator and X-ray inspection apparatus having excellent reliability.

Solution to Problem

An X-ray generator according to a first aspect of the present invention includes an X-ray tube with an anode electrode and a cathode electrode, and a tank housing the X-ray tube and having insulation oil and/or a solid insulator contained therein, and the anode electrode and the cathode electrode are supplied with a predetermined voltage to generate X-ray. The X-ray generator has an abnormal discharge detection unit, an information output unit, and a notification control unit. The abnormal discharge detection unit is configured and arranged to detect individually a first discharge and a second discharge. The first discharge is abnormal discharge inside the X-ray tube. The second discharge is abnormal discharge inside the tank outside the X-ray tube. The information output unit is configured and arranged to output a notification information to the administrator. The notification information is information prompting the replacement of an X-ray tube or a tank. The notification control unit configured and arranged to cause the information output unit to output the notification information in accordance with the detection result by the abnormal discharge detection unit.

As for the "abnormal discharge" bore, included are the abnormal discharge due to the lapse of service life (discharge occurring inside the X-ray tube or inside the tank outside the X-ray tube due to the deterioration of vacuum degree or deterioration of insulation performance of the insulation oil etc.) and the abnormal discharge caused by the structure of the X-ray tube (discharge that can occur inside the X-ray tube, for example due to the fact that electrons emitted from the cathode electrode stay in the X-ray tithe without colliding with the anode electrode).

In the X-ray generator, according to a first aspect of the present invention, the abnormal discharge detection unit individually detects the first discharge and the second discharge and the notification control unit causes the information output unit to output the notification information according to the detection result by the abnormal discharge detection unit. Thus, the first discharge which is the abnormal discharge inside the X-ray tube and the second discharge which is the abnormal discharge inside the tank outside the X-ray tube are individually detected and notification is carried out according to the detection result. As a result, when abnormal discharge occurs inside the tank outside the X-ray tube (that is, abnormal discharge due to the lapse of service life), it becomes possible to prompt maintenance by notifying the administrator. That is, a situation in which notification to the administrator not being accurately performed even when the X-ray tube or the like reaches its replacement time is restrained to occur. Namely, using the apparatus without performing maintenance in a situation where it is assumed that the service life has elapsed can be prevented. Therefore, the decline of inspection accuracy is restrained and reliability is excellent.

In addition, when abnormal discharge occurs, it is possible to output the notification information depending on whether it is the first discharge or the second discharge. For example, it is possible that notification is performed immediately when a second discharge occurs, and when a first discharge occurs, notification is not performed immediately but performed only when the abnormal discharge that occurred is specified as abnormal discharge due to the lapse of service life. That is, when abnormal discharge occurs, notification may be performed when the abnormal discharge is due to the lapse of service life and not perform notification if the abnormal discharge is caused by the structure of the X-ray tube. Consequently, it is possible to accurately perform notification only when necessary, and reliability is also excellent with respect to the accuracy of notification.

An X-ray generator according to a second aspect of the present invention is the X-ray generator according to the first aspect, wherein the notification control unit causes the information output unit to output the notification information when the second discharge is detected by the abnormal discharge detection unit.

As a result of this, when the second discharge occurs (that is, when abnormal discharge due to the lapse of service life occurs), the administrator is immediately notified. Consequently, the X-ray generator is capable of appropriately prompting maintenance such as replacement of the X-ray tube and/or the tank to the administrator, thereby the decline of inspection accuracy is restrained.

An X-ray generator according to a third aspect of the present invention is the X-ray generator according to the first aspect or the second aspect, wherein when the first discharge is detected by the abnormal discharge detection unit, the notification control unit causes the information output unit not to output the notification information when the number of occurrences of the first discharge within a predetermined period is less than a first threshold value. When the first discharge is detected by the abnormal discharge detection unit, the notification control unit causes the information output unit to output the notification information when the number of occurrences of the first discharge within the predetermined period is equal to or greater than the first threshold value. As a result, when the first discharge occurs, notification is performed only when it is specified that the abnormal discharge is due to lapse of service life.

That is, the frequency at which the first discharge occurs (that is, the frequency of occurrence of abnormal discharge in the X-ray tube) increases as the usable period of the X-ray tube or tank approaches service life (replacement time). Therefore, it is possible to determine whether or not the generated first discharge is an abnormal discharge caused by the lapse of the service life based on the frequency of occurrence of the first abnormal discharge and to determine the necessity of maintenance. Therefore, notification is accurately performed only when necessary, and the administrator is properly prompt to perform maintenance such as replacing the X-ray tube and tank.

Note that the "predetermined period" and "first threshold value" herein are appropriately selected depending on the design specification and the operating environment to determine whether or not the frequency of occurrence of the first discharge is large enough to estimate the lapse of the service life of the X-ray tube, that is, whether or not the first discharge has occurred as an abnormal discharge resulting from the lapse of service life.

An X-ray generator according to a fourth aspect of the present invention is the X-ray generator according to any one of the first aspect to the third aspect, wherein the abnormal discharge detection unit detects the first discharge based on a change in the value of the current or the voltage in both of a first electric circuit and a second electric circuit. The first electric circuit is an electric circuit including an anode electrode. The second electric circuit is an electric circuit including a cathode electrode. The abnormal discharge detection unit detects the second discharge based on a change in the value of the current or the voltage in either the first electric circuit or the second electric circuit.

Thus, the first discharge is detected on the basis of the change in the value of the current or the voltage in both the first electric circuit and the second electric circuit, and the second discharge is detected on the basis of the change in the value of the current or voltage in either the first electric circuit or the second electric circuit. That is, when a first discharge (abnormal discharge in the X-ray tube) occurs, a change in the value of the current or the voltage occurs in both the first electric circuit and the second electric circuit, and when a second discharge (abnormal discharge inside the tank outside the X-ray tube) occurs, a change in the value of the current, or voltage occurs in either the first electric circuit or the second electric circuit: based upon this, when abnormal discharge occurs, the first discharge and the second discharge are individually detected in accordance with whether a change in the value of the current or the voltage has occurred in one of the first electric circuit or the second electric circuit, or whether a change in the value of the current or the voltage occurred in both the first electric circuit and the second electric circuit. As a result, it is possible to individually detect the first discharge and the second discharge with high accuracy.

An X-ray inspection apparatus according to a fifth aspect of the present invention includes the X-ray generator according to any one of the first aspect to the fourth aspect, a control unit, an X-ray detection unit, and an image generating unit. The control unit is configured and arranged to control the operation of the X-ray generator. The X-ray detection unit configured and arranged to detect transmitted X-rays. The transmitted X-rays are an X-rays generated by the X-ray generator and transmitted through an inspection target. The image generation unit configured and arranged to generate an image in accordance with the transmitted X-rays detected by the X-ray detection unit.

Consequently, the X-ray inspection apparatus is capable of notifying the administrator to perform maintenance accordingly when the X-ray tube or the like of the X-ray generator reaches its replacement time due to the lapse of service life. Therefore, the decline of inspection accuracy is restrained, and reliability is excellent.

In addition, the X-ray inspection apparatus is capable of accurately notifying the administrator to prompt maintenance only when it is necessary. Therefore, reliability is also excellent with respect to accuracy of notification.

Advantageous Effects of Invention

In the X-ray generator according to the present invention, the first discharge which is the abnormal discharge in the X-ray tube and the second discharge which is the abnormal discharge inside the tank outside the X-ray tube are individually detected to perform notification according to the detection result. As a result, when abnormal discharge occurs inside the tank outside the X-ray tube (that is, abnormal discharge due to the lapse of service life), it is possible to notify the administrator and prompt maintenance. That is, a situation in which notification to the administrator not being accurately performed even when the X-ray tube or the like reaches its replacement time is restrained to occur. Namely, using the apparatus without performing maintenance in a situation where it is assumed that the service life has elapsed can be prevented. Therefore, the decline of inspection accuracy is restrained and reliability is excellent.

In addition, when abnormal discharge occurs, it is possible to output the notification information depending on whether it is the first discharge or the second discharge. For example, it is possible that notification is performed immediately when a second discharge occurs, and when a first discharge occurs, notification is not performed immediately but performed only when the abnormal discharge that occurred is specified as abnormal discharge due to the lapse of service life. That is, when abnormal discharge occurs, notification may be performed when the abnormal discharge is due to the lapse of service life and not perform notification if the abnormal discharge is caused by the structure of the X-ray tube. Consequently, it is possible to accurately perform notification only when necessary, and reliability is also excellent with respect to the accuracy of notification.

BRIEF DESCRIPTION OF THE DRAWINGS

FIG. 2 is a perspective view of the external appearance of an X-ray inspection unit.

DESCRIPTION OF EMBODIMENTS

Hereinafter, an inspection sorting apparatus 100 (X-ray generator, X-ray inspection apparatus) according to an embodiment of the present invention will be described with reference to the drawings. The embodiment described below is a specific example of the present invention and does not limit the technical scope of the present invention. It is therefore understood that numerous modifications and variations can be devised without departing from the scope of the invention.

(1) OVERVIEW OF INSPECTION SORTING APPARATUS 100

Figure 1:
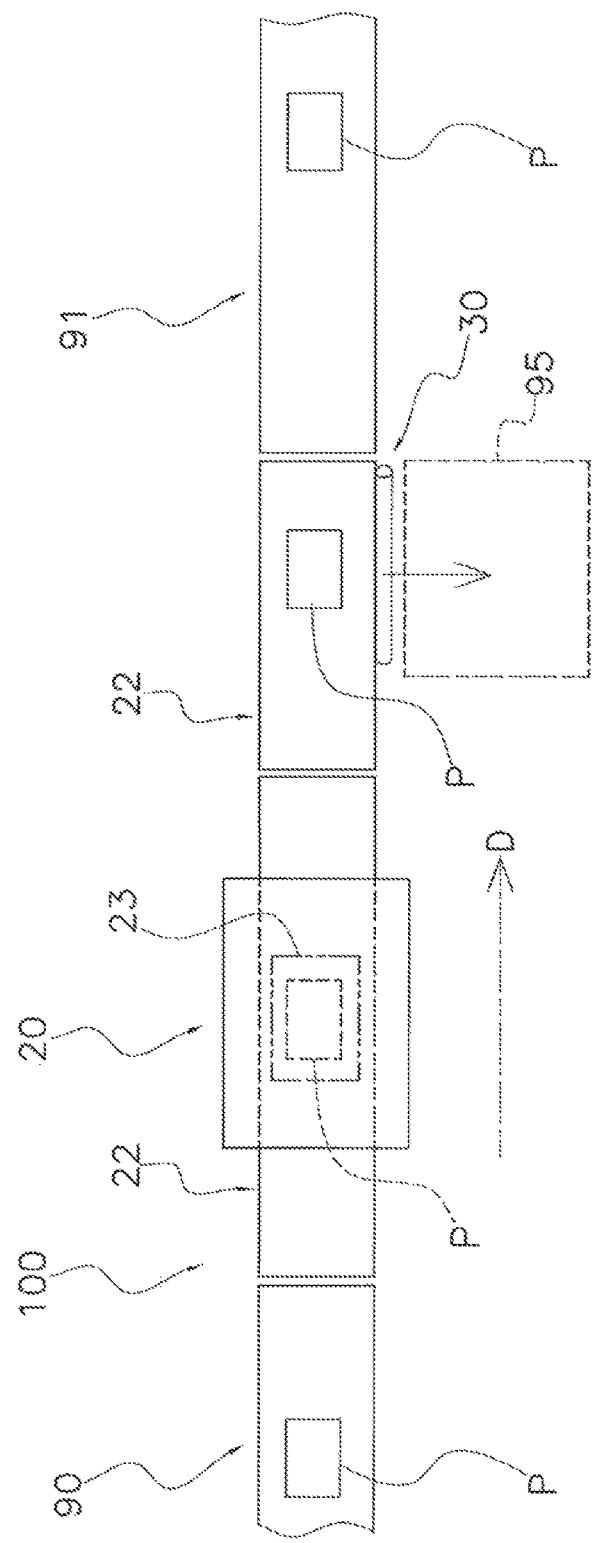
FIG. 1 is a schematic view of an inspection sorting apparatus according to an embodiment of the present invention.

FIG. 1 is a schematic view of the inspection sorting apparatus 100 according to an embodiment of the present invention. In the present embodiment, the inspection sorting apparatus 100 is a system that performs quality inspection of articles P (article to be inspected) that are food (processed foods, fresh food items, etc.) and sorts them into non-defective and defective products. In particular, as quality inspection, the inspection sorting apparatus 100 performs foreign matter inspection (inspection regarding whether the articles P are contaminated with foreign matter). Note that the articles P are not necessarily limited to food products but may be other items (for example, industrial products, medicines, etc.).

The inspection sorting apparatus 100 is incorporated in a production line for carrying articles P in the conveyance direction D (refer to the two-dot chain line arrow in FIG. 1) to perform various processing such as manufacturing, measuring, packaging, and packing of articles P. The inspection sorting apparatus 100 is connected to an upstream-side conveyor 90 at the end section on the side that receives the articles P and is connected to a downstream-side conveyor 91 at the end section on the side that sends out the articles P. The inspection sorting apparatus 100 irradiates X-rays to the articles P that are conveyed at a predetermined interval along the upstream-side conveyor 90, and performs quality inspection of the articles P based on X-rays (transmitted X-rays) transmitted through the articles P and determines whether or not the articles P are defective in accordance with the inspection result. In the present embodiment, the inspection sorting apparatus 100 performs contaminant inspection for inspecting the presence or absence of contaminants of foreign matter in each of the articles P based on the transmitted X-rays, and concludes that an article P determined to be contaminated with foreign matter is a defective product.

The inspection sorting apparatus 100 sends the articles P determined as non-defectives (that is, good products) to the downstream-side conveyor 91. The inspection sorting apparatus 100 sends the articles P determined to be defective to a defective product collection box 95 and excludes the defective products from the production line by sorting them from the articles P (good products) that are to be sent to the downstream-side conveyor 91.

(2) DETAILED DESCRIPTION OF INSPECTION SORTING APPARATUS 100

The inspection sorting apparatus 100 mainly includes an X-ray inspection unit 20 for inspecting the article P and determining whether or not the articles P are defective, a sorting unit 30 for sorting non defective products among the articles P after inspection, and a controller 40 (see FIG. 7) for controlling the operations of the X-ray inspection unit 20 and the sorting unit 30.

(2-1) X-Ray Inspection Unit 20

FIG. 2 is a perspective view of the external appearance of the X-ray inspection unit 20. The X-ray inspection unit 20 mainly includes a shield box 21, a conveyor unit 22, an X-ray irradiator 23, a line sensor 24 (see FIG. 3), and an LCD display 25.

(2-1-1) Shield Box 21

The shield box 21 is a casing that houses various devices (specifically, the conveyor unit 22, the X-ray irradiator 23, the line sensor 24, or the like) constituting the X-ray inspection unit 20. The controller 40 is also accommodated in the shield box 21. Furthermore, the LCD display 25, a key insertion opening, a power switch, and the like are disposed in the upper front part of the shield box 21.

The shield box 21 has openings 21a for transporting articles P into and out of the shield box 21. The openings 21a are located on the side surfaces of the shield box 21 on the upstream side and downstream side in the conveyance direction D. The openings 21a are each covered with a shield curtain 26 for reducing X-ray leakage to the exterior of the shield box 21. The shield curtain 26 is made of tungsten-containing rubber. The shield curtain 26 is pushed aside by the articles P conveyed by the conveyor unit 22 when the articles P are carried into the shield box 21 or when the articles P are carried out of shield box 21.

(2-1-2) Conveyor Unit 22

The conveyor unit 22 transports the articles P received from the upstream-side conveyor 90 to the inside of the shield box 21, and to the sorting unit 30 on the downstream side after passing through the inside of the shield box 21. The conveyor unit 22 is disposed so as to pass through the openings 21a on both side surfaces of the shield box 21.

The conveyor unit 22 mainly has an inverter-type conveyor motor 22a (see FIG. 7), an encoder 22b (see FIG. 7), conveyor rollers 22c, and an endless conveyor belt 22d. The output terminal of the conveyor motor 22a is connected to the conveyor rollers 22c. The conveyor rollers 22e are driven in conjunction with and by the conveyor motor 22a. The conveyor rollers 22c are driven to rotate the conveyor belt 22d and convey the articles P on the conveyor belt 22d to the downstream side (toward the sorting unit 30 side).

The encoder 22b is mounted on the conveyor motor 22a. The encoder 22b detects the rotation speed of the conveyor motor 22a and transmits the detection results to the controller 40.

The transport speed of the conveyor unit 22 is precisely controlled through an inverter-control of the conveyor motor 22a by the controller 40, so as to match the transport speed with the setting speed input by an operator to the LCD display 25.

(2-1-3) X-Ray Irradiator 23

Figure 3:
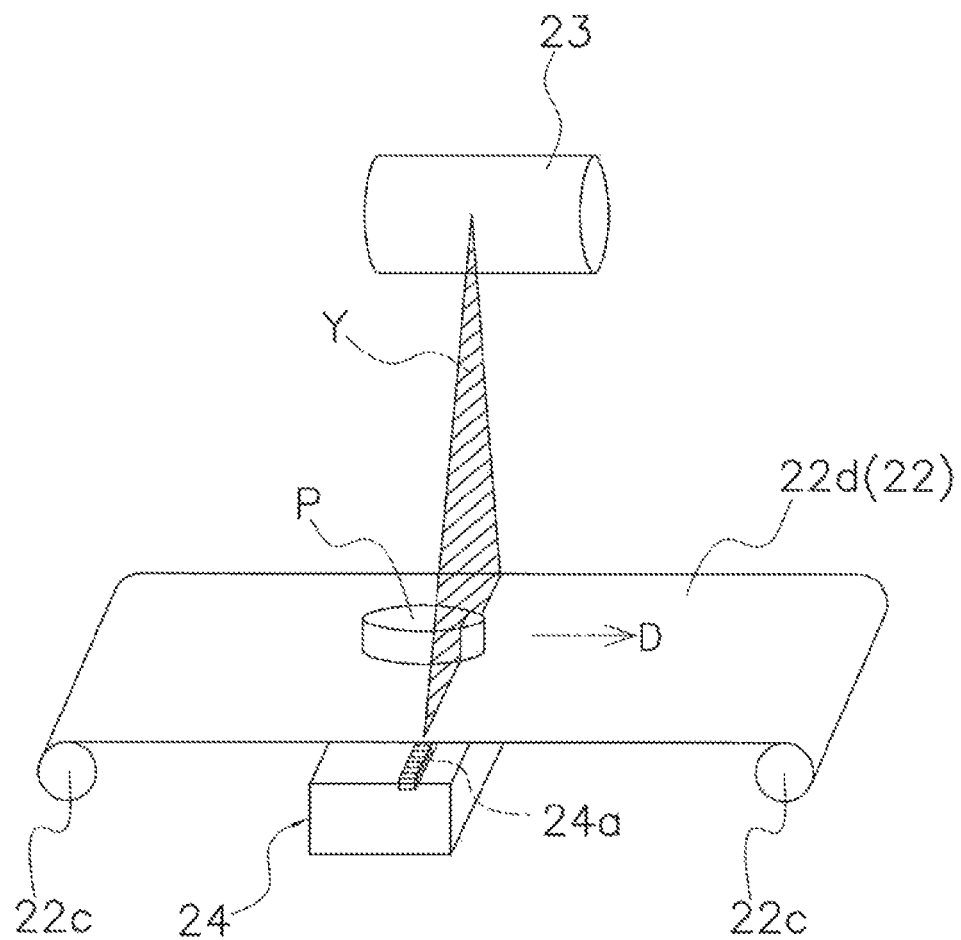
FIG. 3 is a schematic view of the interior of a shield box.

FIG. 3 is a schematic view of the interior of the shield box 21. The X-ray irradiator 23 is disposed above the line sensor 24 and the conveyor unit 22. The X-ray irradiator 23 generates X-rays inside the shield box 21 and irradiates X-rays toward an article P transported therein. More specifically, the X-ray irradiator 23 irradiates X-rays in a fan-shaped irradiation range Y (see the hatched portion in FIG. 3) toward the line sensor 24 disposed below the conveyor unit 22. The irradiation range Y extends vertically with respect to the conveying surface of the conveyor unit 22. Also, the irradiation range Y widens in the direction orthogonal to, the conveyance direction D of the article P (that is, the width direction of the conveyor belt 22d).

Details of the X-ray irradiator 23 will be described later.

(2-1-4) Line Sensor 24 (X-Ray Detection Unit)

Disposed below the conveyor belt 22d, the line sensor 24 detects X-rays (transmitted X-rays) transmitted through the article P and the conveyor belt 22d, and outputs an X-ray fluoroscopic image signal (see FIG. 8) corresponding to the detection result to the controller 40. In other words, the line sensor 24 outputs the X-ray transmission signals that correspond to the intensity of the transmitted X-rays to the controller 40. The intensity of the transmitted X-rays depends on the amount of transmitted X-rays. It is to be noted that although an X-ray image that is generated by the controller 40 (the X-ray image generation unit 44 to be described later) based on the X-ray transmission signal (that is, the intensity of the transmitted X-rays) will be described later, the brightness (luminance) of the generated X-ray image is determined based on the X-ray transmission signals outputted by the line sensor 24.

The line sensor 24 includes numerous X-ray detection elements 24a (pixel sensors) installed in a straight line in the width direction of the conveyor belt 22d in an orientation orthogonal to the conveyance direction D of the articles P. In the present embodiment, the X-ray detection element 24a is a photodiode and is mounted on a substrate.

Figure 8:
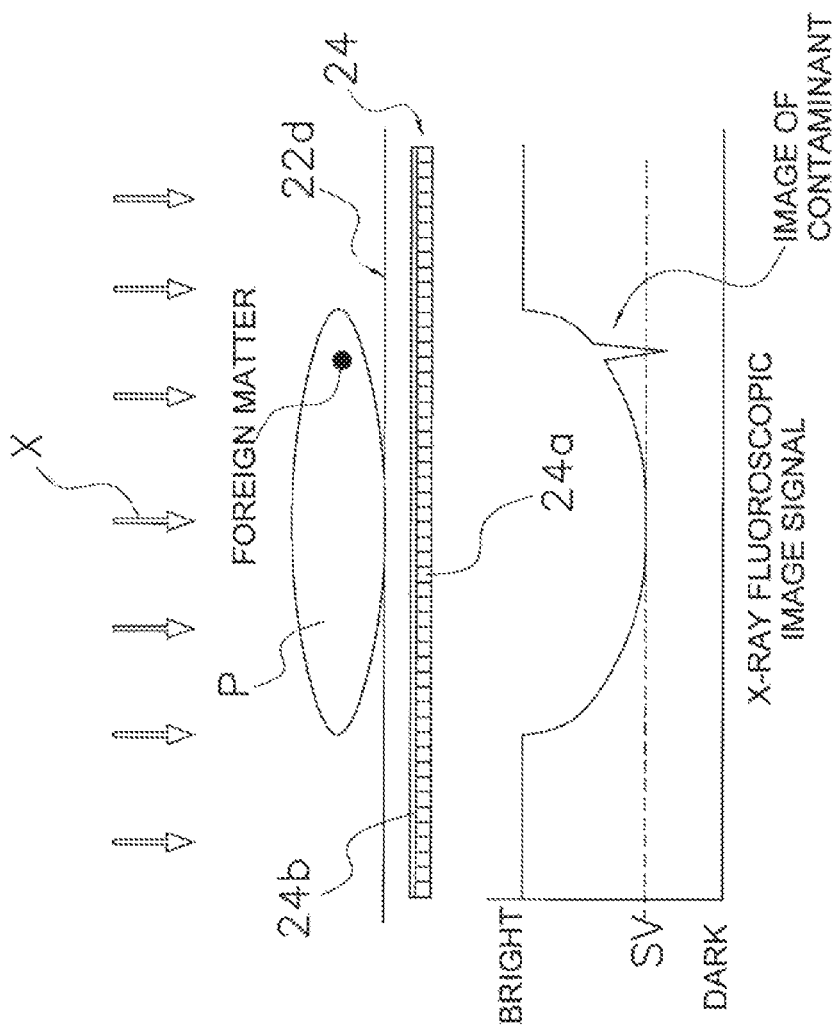
FIG. 8 is a schematic diagram depicting a correspondence relation between X-ray fluoroscopic image signals and brightness (luminance) of an X-ray image generated by an X-ray image generation unit.

The line sensor 24 further includes a scintillator 24b (see FIG. 8). The scintillator 24b is disposed on the X-ray detection element 24a. In the present embodiment, fluorescent paper is used as the scintillator 24b. The scintillator 24b converts incident X-rays from above into light and renders the converted light to enter the X-ray detection elements 24a disposed thereunder.

The X-ray detection element 24a generates a current according to the amount of light incident from the scintillator 24b, accumulates the electric charge, converts the accumulated electric charge into electric signal, and outputs it as the X-ray fluoroscopic image signal to the controller 40.

Note that the line sensor 24 also functions as a sensor for detecting the timing at which the article P passes through the irradiation range Y of the X-rays. More specifically, when the article P conveyed by the conveyor unit 22 has arrived at the position (irradiation range Y) above the line sensor 24, any one of the X-ray detection elements 24a of the line sensor 24 outputs an X-ray transmission signal (first signal) indicating a voltage that is equal to or less than a predetermined threshold value. Also, when the article P has finished passing through the irradiation range Y all of the X-ray detection elements 24a of the line sensor 24 output an X-ray transmission signal (second signal) indicating a voltage above the predetermined, threshold value. The first and second signals are input to the controller 40, whereby the presence of an article P in the irradiation range Y is detected.

(2-1-5) LCD Display 25 (Information Output Unit)

The LCD display 25 is a liquid crystal display (so-called touch screen) having a touch panel (input means capable of touch input). The LCD display 25 is electrically connected to the controller 40 and exchanges signals with the controller 40.

The LCD display 25 functions as a display unit that displays (outputs) information to an administrator and as an input unit through which the administrator inputs various commands. The LCD display 25 displays the information generated by the controller 40. For example, the LCD display 25 displays X-ray images (described later) and notification information (described later) and the like outputted from the controller 40.

(2-2) Sorting Unit 30

Figure 4:
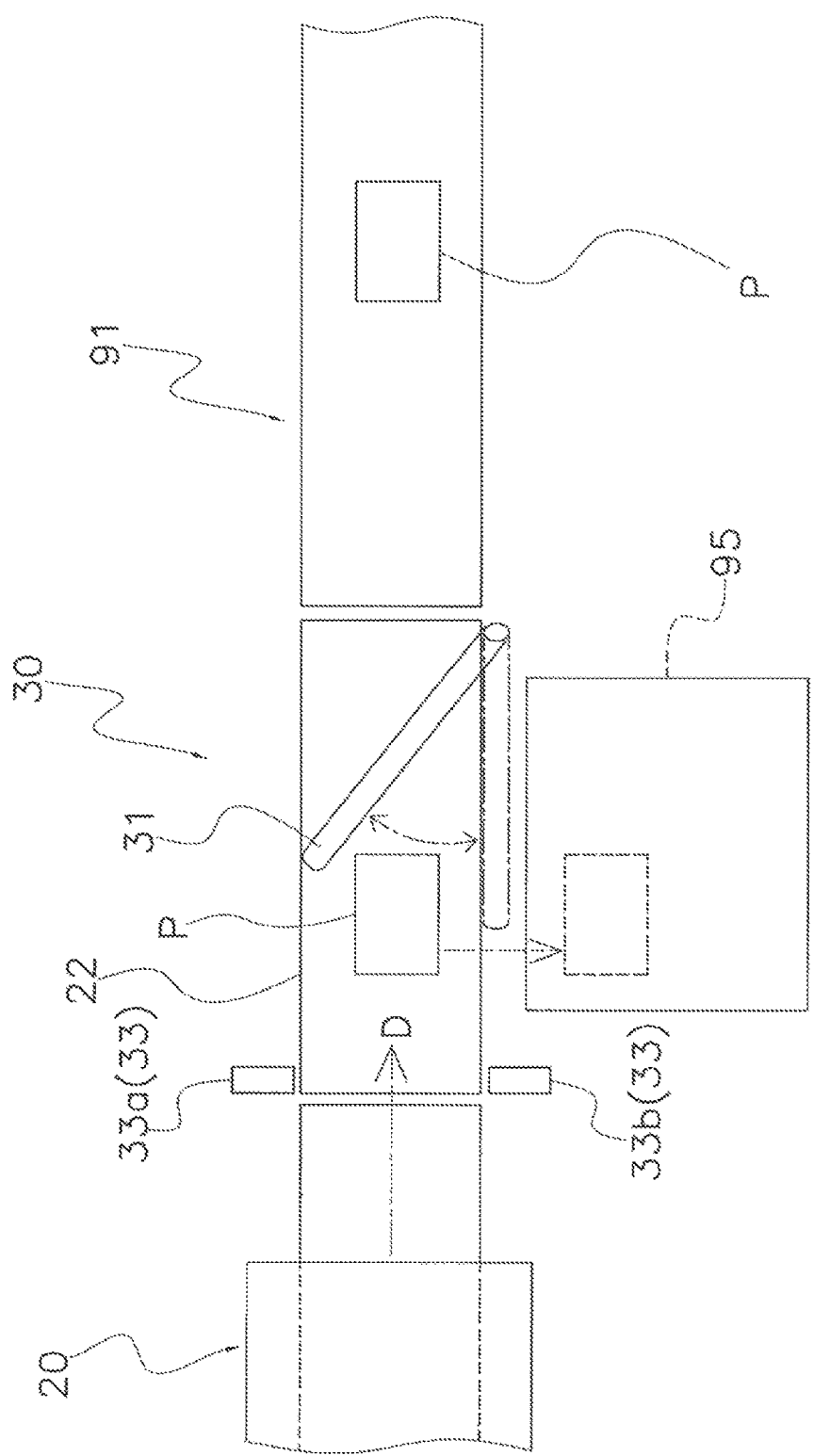
FIG. 4 is a schematic diagram illustrating a state in which a sorting unit (arm) is operated and articles are sent to a defective product collection box.

FIG. 4 is a schematic diagram illustrating a state in which the sorting unit 30 (arm 31) is operated and articles P are sent to a defective product collection box 95. In accordance with a command from the controller 40, the sorting unit 30 sends defective products from among the articles P being conveyed to the defective product collection box 95.

The sorting unit 30 mainly includes an arm 31 for sending defective products transported by the conveyor unit 22 to the defective product collection box 95, an arm driving unit 32 (see FIG. 7) for driving the arm 31, and a photoelectric sensor 33 for detecting the articles P on the upstream side of the arm 31.

The arm 31 has a rotation shaft attached to side portion of the conveyor unit 22. The arm driving unit 32 is connected to the rotation shaft of the arm 31, and the arm 31 moves in conjunction with the operation of the arm driving unit 32. Specifically, the arm 31 moves between a position (indicated by a one-dot chain line in FIG. 4) along the conveyance direction D of article P and a sorting position (position indicated by a solid line in FIG. 4) diagonally shielding the article P (see one-dot chain line arrow in FIG. 4). The arm 31 moves in this manner according to the timing when a defective product is conveyed in order to remove the defective product from the conveyor unit 22 and send it to the defective product collection box 95 that is disposed near the side of the conveyor unit 22.

The arm driving unit 32 includes an actuator such as an air cylinder or a motor, and the driving thereof is controlled by the controller 40.

The photoelectric sensor 33 includes a light projector 33a for irradiating light and a light receiver 33b for receiving the irradiated light. The photoelectric sensor 33 is electrically connected to the controller 40. The operation of the light projector 33a is controlled by the controller 40. When receiving the light irradiated from the light projector 33a, the light receiver 33b outputs a predetermined signal (light reception signal) to the controller 40 whereas when not receiving light, the light receiver 33b stops outputting the light reception signal to the controller 40. As a result, the controller 40 detects the timing at which the article P passes through the sorting unit 30.

(2-3) Controller 40

The controller 40 is a computer mainly has a CPU (Central Processing Unit), a ROM (Read Only Memory), a RAM (Random Access Memory), an HDD (Hard Disk Drive), and the like. The controller 40 controls the operation of each device included in the X-ray inspection unit 20. Further, the controller 40 performs inspection (foreign matter inspection) on whether or not the article P is defective based on the detection results of the amount of transmitted X-rays by the line sensor 24. In addition, as a result of the foreign matter inspection, the controller 40 drives the sorting unit 30 so as to exclude the article P determined as a defective product from the production line, and to collect the article P into the defective product collection box 95. In addition, the controller 40 determines whether maintenance, such as replacement of an X-ray tube 50 or a tank 53 is necessary or not, and notifies the administrator to prompt such maintenance according to the determination result.

Details of the controller 40 will be described later.

(3) DETAILED DESCRIPTION OF X-RAY IRRADIATOR 23

Figure 5:
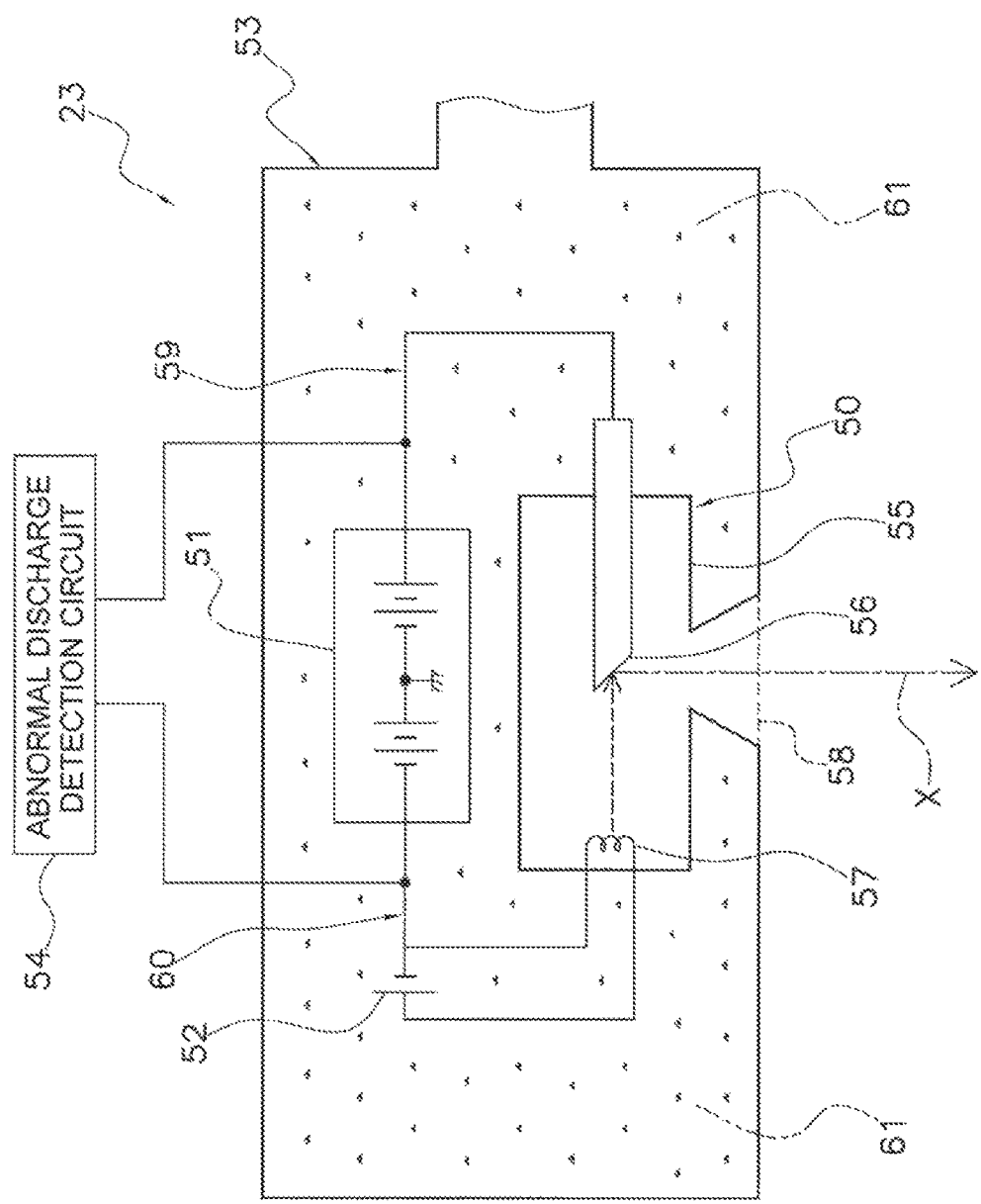
FIG. 5 is a schematic diagram schematically illustrating an X-ray irradiator.

FIG. 5 is a schematic diagram schematically illustrating, the X-ray irradiator 23. The X-ray irradiator 23 has an X-ray tube 50, a high voltage power supply 51, a filament power supply 52, a tank 53, and an abnormal discharge detection circuit 54.

The X-ray tube 50 includes an X-ray tube main body 55 made of stainless steel and ceramics, and an anode electrode 56 (X-ray target) and a cathode electrode 57 (filament) both disposed inside the X-ray tube main body 55. The X-ray tube main body 55 has an X-ray irradiation window 58 that transmits X-rays.

The high voltage power supply 51 is connected to a power supply (not shown) (for example, a commercial AC power supply or a DC power supply), and boosts the input voltage with an inverter or the like (not shown) to generate a high voltage DC voltage. With a positive output terminal connected to the anode electrode 56 and a negative output terminal connected to the cathode electrode 57, the high voltage power supply 51 supplies a predetermined voltage to each of the anode electrode 56 and the cathode electrode 57 to thereby generate a potential difference between the anode electrode 56 and the cathode electrode 57. In the present embodiment, the high voltage power supply 51 generates a potential difference of 100 kV between the anode electrode 56 and the cathode electrode 57. Note that the potential difference generated between the anode electrode 56 and the cathode electrode 57 by the high voltage power supply 51 is not necessarily limited to 100 kV and may be appropriately changed in accordance with the design specifications and operating environment.

The filament power supply 52 supplies a heating current to the cathode electrode 57. When the heating current is supplied from the filament power supply 52 to the cathode electrode 57 in state in which a predetermined potential difference is generated between the anode electrode 56 and the cathode electrode 57 (that is, a state in which a predetermined voltage is supplied from the high voltage power supply 51 to the anode electrode 56 and the cathode electrode 57) as mentioned above, the cathode electrode 57 is heated, thereby emitting thermoelectrons from the cathode electrode 57, and the emitted thermoelectrons from the cathode electrode 57 collide with the anode electrode 56 (sec the broken line arrow in FIG. 5) in the X-ray tube 50. As a result, X-rays to be irradiated to the outside of the X-ray tube 50 through the X-ray irradiation window 58 are generated (see the one-dot chain line arrow X in FIG. 5). Note that in order to irradiate the X-rays properly toward the X-ray irradiation window 58, the anode electrode 56 is disposed so that the angle of incidence of thermoelectrons emitted from the cathode electrode 57 is at an appropriate angle.

The tank 53 accommodates the X-ray tube 50, the high voltage power supply 51, and the filament power supply 52. Furthermore, disposed in the tank 53 are a first electric circuit 59 which is an electric circuit connecting the high voltage power supply 51 to the anode electrode 56 (that is, an electric circuit including the anode electrode 56), and a second electric circuit 60 which is an electric circuit connecting the high voltage power supply 51 to the cathode electrode 57 (that is, an electric circuit including the cathode electrode 57).

Further, insulation oil 61 is filled in the tank 53. The insulation oil 61 has electrical insulation properties to ensure an electrically insulated state between respective components that have a potential difference in the space inside the tank 53 (for example, between the first electric circuit 59 and the second electric circuit 60 or between the first electric circuit 59 or the second electric circuit 60 and the tank 53 or the X-ray tube main body 55). In addition, the insulation oil 61 plays a role of cooling the X-ray tube 50 that generates high heat when generating X-rays. Inside the tank 53, a solid insulator (not shown) such as epoxy or silicone may be sealed (instead of the insulation oil 61/together with the insulation oil 61).

The abnormal discharge detection circuit 54 is a circuit for detecting abnormal discharge occurring inside the X-ray tube 50 (X-ray tube main body 55) or abnormal discharge occurring inside the tank 53 and outside the X-ray tube 50.

Here, the "abnormal discharge" refers to a discharge which can be an obstacle to the inspection in the inspection sorting apparatus 100. Such abnormal discharge includes abnormal discharge caused by the structure of the X-ray tube 50 and abnormal discharge caused by the lapse of service life of the X-ray tube 50 or the insulation oil 61 and the like.

The abnormal discharge caused by the structure of the X-ray tube 50 is due to the fact that electrons emitted from the cathode electrode 57 stay inside the X-ray tube 50 without colliding with the anode electrode 56, and occurs inside the X-ray tube 50, thus, has little relevance to the course of service life. More specifically, discharge caused between the anode electrode 56 and cathode electrode 57 because gas inside the X-ray tube 50 is ionized by electrons or the like emitted from the cathode electrode 57, and discharge caused in the X-ray tube 50 because the electrons emitted, from the cathode electrode 57 temporarily accumulate and saturate on X-ray tube wall maintaining insulation, for example, correspond to the abnormal discharge caused by the structure of the X-ray tube 50.

Abnormal discharge due to the lapse of service life may occur inside the X-ray tube 50 or inside the tank 53 outside the X-ray tube 50 due to the deterioration of the degree of vacuum and/or the deterioration of the insulation performance of the insulation oil 61.

Note that in the following description, for convenience of explanation, abnormal discharge in the X-ray tube 50 is referred to as "first abnormal discharge" and abnormal discharge inside the tank 53 outside the X-ray tube 50 is referred to as "second abnormal discharge".

Figure 6:
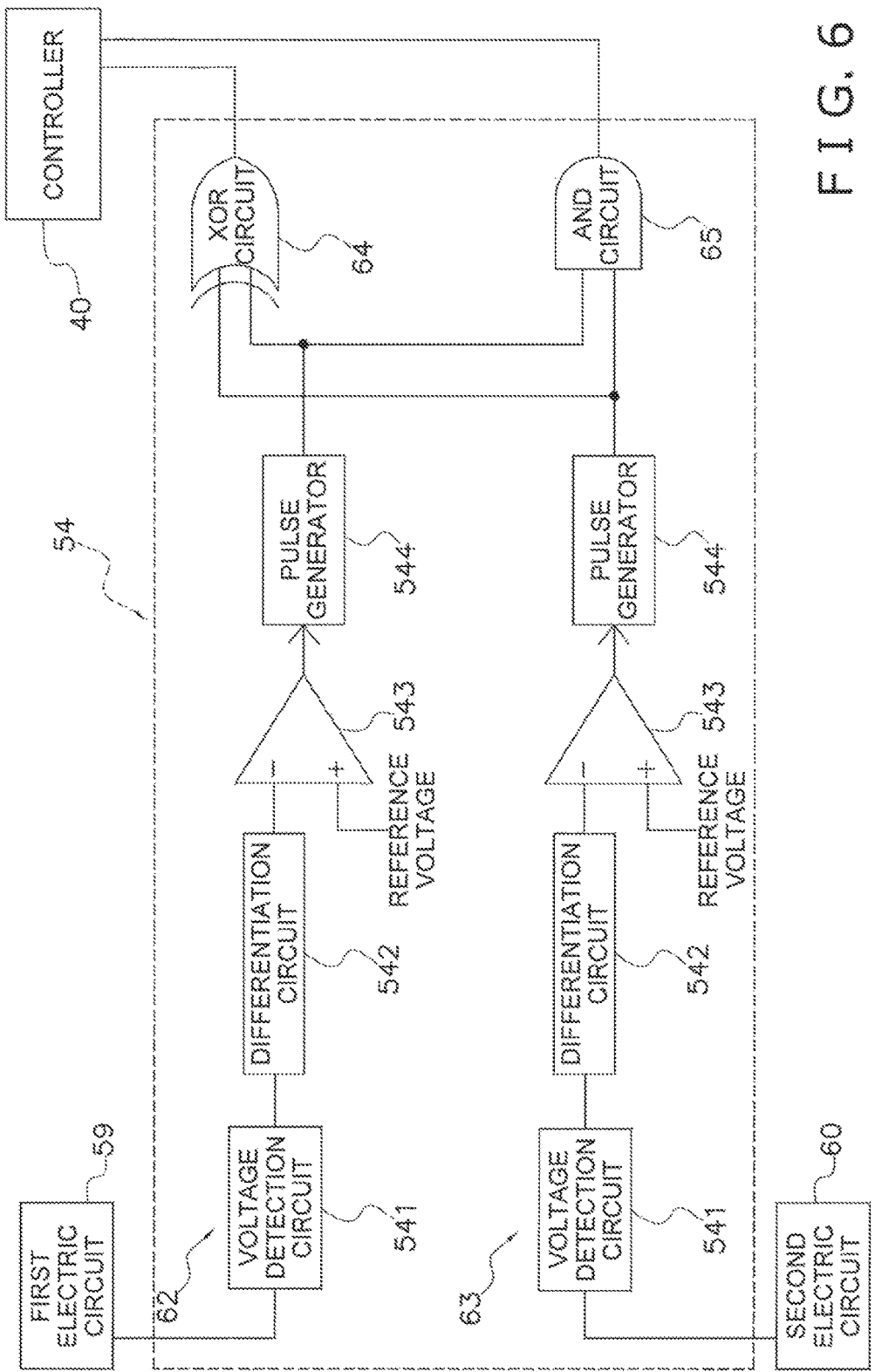
FIG. 6 is a schematic diagram schematically illustrating an abnormal discharge detection circuit.

FIG. 6 is a schematic diagram schematically illustrating an abnormal discharge detection circuit 54. The abnormal discharge detection circuit 54 is connected to the first electric circuit 59, the second electric circuit 60, and the controller 40, respectively. The abnormal discharge detection circuit 54 includes a first detection unit 62 for outputting a pulse in accordance with a change (a sudden drop) in the voltage value in the first electric circuit 59, a second detection unit 63 for outputting a pulse in response to a change (a sudden drop) in the voltage value in the second detection unit 63, an XOR circuit 64, and an AND circuit 65.

Each of the first detection unit 62 and the second detection unit 63 includes a voltage detection circuit 541, a differentiation circuit 542, a comparator 543, and a pulse generator 544 that are successively connected in series. The voltage detection circuit 541 is connected to the first electric circuit 59 or the second electric circuit 60 at the input side. The voltage detection circuit 541 is connected to the differentiation circuit 542 at the output side. The output side of the differentiation circuit 542 is connected to the negative input terminal of the comparator 543. The comparator 543 is connected to a reference power supply (not shown) at the positive input terminal, and is supplied with a reference voltage. The comparator 543 is connected to the pulse generator 544 at the output side. The pulse generator 544 is connected to the XOR circuit 64 and the AND circuit 65 at the output side.

In the first detection unit 62 and the second detection unit 63, the voltage detection circuit 541 detects a value (voltage value) of the voltage supplied to the connected circuit (that is, the first electric circuit 59 or the second electric circuit 60). The differentiation circuit 542 and the comparator 543 detect a change (a sudden drop) in the voltage value supplied to the first electric circuit 59 or the second electric circuit 60 based on the detection result of the voltage detection circuit 541. Based on the output of the comparator 543, the pulse generator 544 outputs a pulse when a change (a sudden drop) in the voltage value supplied to the first electric circuit 59 or the second electric circuit 60 occurs.

The XOR circuit 64 and the AND circuit 65 are connected to the controller 40 at the output side. When a pulse is input from only one of the first detection unit 62 and the second detection unit 63 (that is, when the voltage value changes (a sudden drop) in one of the first electric circuit 59 and the second electric circuit 60), the XOR circuit 64 outputs a signal (XOR signal) to the controller 40. When pulses are input from both of the first detection unit 62 and the second detection unit 63 (that is, when a change (a sudden drop) in the voltage value occurs in both the first electric circuit 59 and the second electric circuit 60), the AND circuit 65 outputs a signal (AND signal) to the controller 40.

The abnormal discharge detection circuit 54 configured as described above has a function of detecting a change (a sudden drop) in the voltage value in the first electric circuit 59 and/or the second electric circuit 60 and outputting a signal. Note that the configuration of the abnormal discharge detection circuit 54 is not necessarily limited to the embodiment shown in FIG. 6, but that each element of the circuit can be added, deleted and changed as long as such function is realized. Although the voltage detection circuit 541, the differentiation circuit 542, the comparator 543, the pulse generator 544, the XOR circuit 64, and the AND circuit 65 are shown in a simplified manner in FIG. 6, the abnormal discharge detection circuit 54 may be configured by selecting and combining appropriate electric components to fulfill the functions of the respective units.

(4) DETAILED DESCRIPTION OF CONTROLLER 40

Figure 7:
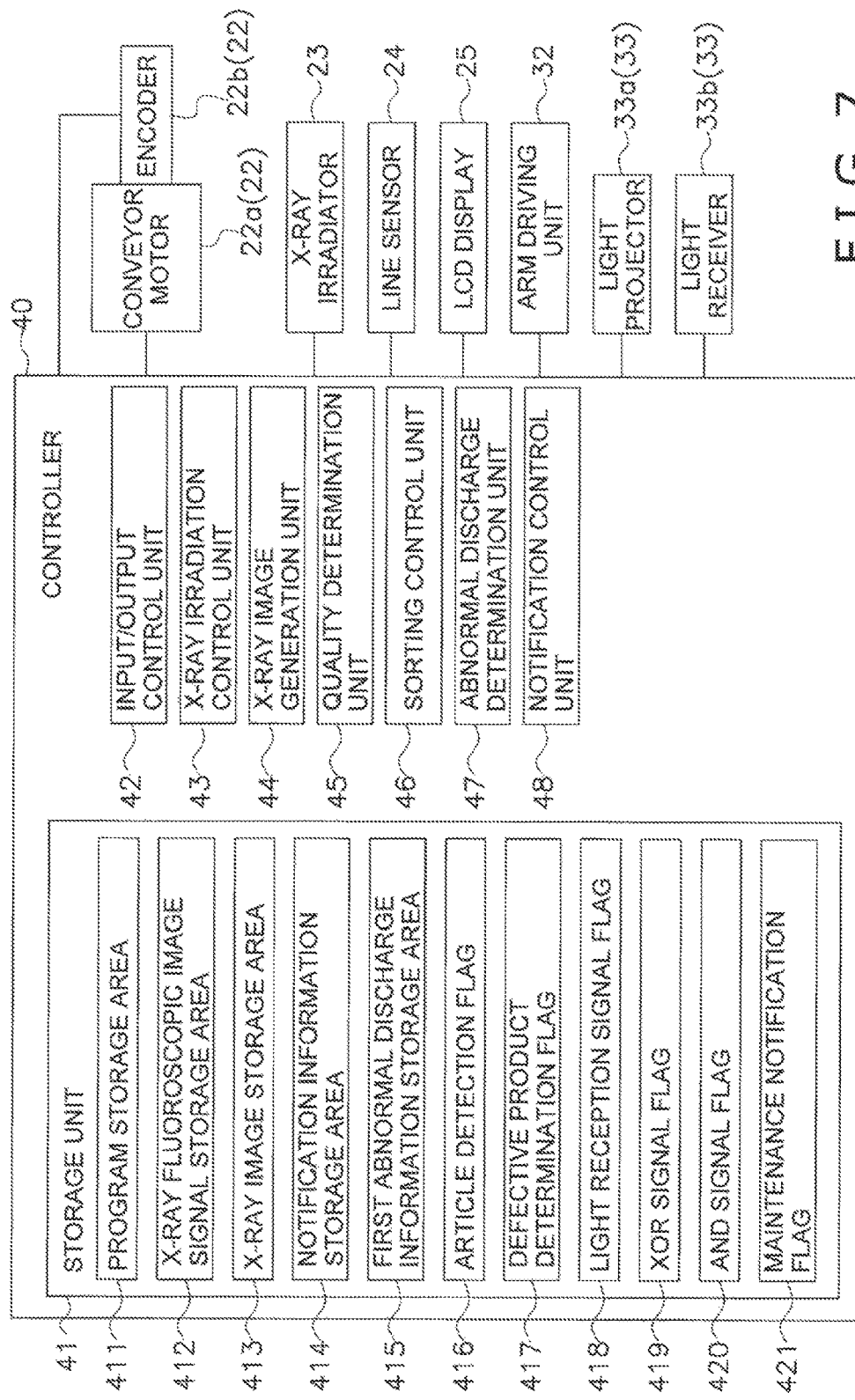
FIG. 7 is a block diagram schematically illustrating a controller and an equipment connected to the controller.

FIG. 7 is a block diagram schematically illustrating the controller 40 and an equipment connected to the controller 40. The controller 40 is mainly electrically connected to the conveyor motor 22a, the encoder 22b, the X-ray irradiator 23, the line sensor 24, the LCD display 25, the arm driving unit 32, the light projector 33a, and the light receiver 33b. The controller 40 mainly includes a storage unit 41, an input/output control unit 42, an X-ray irradiation control unit 43, an X-ray image generation unit 44, a quality determination unit 45, a sorting control unit 46, an abnormal discharge determination unit 47, and a notification control unit 48.

(4-1) Storage Unit 41

The storage unit 41 is configured with a ROM, a RAM, an HDD, a flash memory, and the like, and has a volatile storage area and a nonvolatile storage area. The storage unit 41 mainly includes a program storage area 411 having a predetermined storage capacity, the X-ray fluoroscopic image signal storage area 412, an X-ray image storage area 413, a notification information storage area 414, a first abnormal discharge information storage area 415, an article detection flag 416, a defective product determination flag 417, the light reception signal flag 418, an XOR signal flag 419, an AND signal flag 420, and a maintenance notification flag 421.

The program storage area 411 is an area for storing a control program defining the processes of each of the units (42 to 48) of the controller 40. The X-ray fluoroscopic image signal storage area 412 is an area for storing the X-ray fluoroscopic image signal output from the line sensor 24. The X-ray image storage area 413 is an area for storing the X-ray image (later described) generated by the X-ray image generation unit 44. The notification information storage area 414 is an area, for storing notification information (later described) generated by the notification control unit 48. The first abnormal discharge information storage area 415 is an area for storing a detection time of the first abnormal discharge for a predetermined number of times.

The article detection flag 416 is a flag for determining whether or not an article P has been conveyed into the shield box 21. The defective product determination flag 417 is a flag for determining whether or not the article P passing through the X-ray inspection unit 20 and sent to the sorting unit 30 is defective. The light reception signal flag 418 is a flag for determining that the article P having passed through the X-ray inspection unit 20 has reached the sorting unit 30. The XOR signal flag 419 is a flag for discriminating that the XOR signal is output from the XOR circuit 64 (abnormal discharge detection circuit 54). The AND signal flag 420 is a flag for discriminating that the AND signal is output from the AND circuit 65 (abnormal discharge detection circuit 54). The maintenance notification flag 421 is a flag for determining the timing to notify the administrator of the notification information prompting maintenance such as replacement of the X-ray tube 50 or the tank 53.

(4-2) Input/Output Control Unit 42

The input/output control unit 42 performs controls relating to the input and output of various signals. For example, upon receiving the first signal outputted from the line sensor 24, the input/output control unit 42 sets the article detection flag 416. Furthermore, upon receiving the second signal outputted from the line sensor 24, the input/output control unit 42 clears the article detection flag 416. In addition, the input/output control unit 42 receives the X-ray fluoroscopic image signal outputted from the line sensor 24 and stores the X-ray fluoroscopic image signal in the X-ray fluoroscopic image signal storage area 412. Further, upon receiving the light reception signal outputted from the photoelectric sensor 33, the input/output control unit 42 sets the light reception signal flag 418. The input/output control unit 42 also clears the light reception signal flag 418 when the light reception signal outputted from the photoelectric sensor 33 disappears.

Moreover, when the X-ray image is newly stored in the X-ray image storage area 413, the input/output control unit 42 outputs the new X-ray image to the LCD display 25. Further, when the notification information is newly stored in the notification information storage area 414, the input/output control unit 42 outputs the new notification information to the LCD display 25.

(4-3) X-Ray Irradiation Control Unit 43 (Control Unit)

The X-ray irradiation control unit 43 executes controls relating to the operation of the X-ray irradiator 23. When the article detection flag 416 is set (that is, when the article P is conveyed in the shield box 21 and arrives at an above position (the irradiation range Y) of the line sensor 24), the X-ray irradiation control unit 43 causes the high voltage power supply 51 in the X-ray irradiator 23 to supply a predetermined voltage to the anode electrode 56 and the cathode electrode 57 and causes the filament power supply 52 to supply the heating current to the cathode electrode, whereby X-rays are generated and irradiated onto the article P.

(4-4) X-Ray Image Generation Unit 44 (Image Generation Unit)

The X-ray image generation unit 44 generates the X-ray image based on the latest X-ray fluoroscopic image signal stored in the X-ray fluoroscopic image signal storage area 412. Based on the amount of transmitted X-rays specified by the X-ray fluoroscopic image signal, the X-ray image generation unit 44 generates the X-ray image as a transmission image. More specifically, the X-ray image generation unit 44 generates the X-ray image by chronologically connecting data in every fine intervals related to the intensity of the X-rays obtained from the respective X-ray detection elements 24a in the form of a matrix.

In the X-ray image generated by the X-ray image generation unit 44, locations where a high amount of transmitted X-rays is detected by the X-ray detection elements 24a appear bright (pale, high luminance), and the locations where a low amount of transmitted X-rays rays is detected appear dark (deep, low luminance).

FIG. 8 is a schematic diagram depicting a correspondence relation between the X-ray fluoroscopic image signals and brightness (luminance) of the X-ray image generated by the X-ray image generation unit 44. In the X-ray image generated by the X-ray image generation unit 44, the luminance becomes lower (darker) as the intensity of the transmitted X-rays are smaller and the luminance becomes higher (brighter) as the intensity of the transmitted X-rays are larger. For this reason, in the X-ray image that is generated when the article P is contaminated with foreign matter, as shown in FIG. 8, for the area of the article P contaminated with foreign matter, the luminance becomes lower because the intensity of the transmitted X-rays are smaller, as compared with an area not contaminated with foreign matter. In FIG. 8, the luminance of the area contaminated with foreign matter in the X-ray image is lower than a predetermined reference value SV.

The X-ray image generation unit 44 stores the generated X-ray image in the X-ray image storage area 413. As a result, the generated X-ray image is outputted to the LCD display 25 by the input/output control unit 42 and displayed on the LCD display 25.

(4-5) Quality Determination Unit 45

Based on the latest X-ray image stored in the X-ray image storage area 413, the quality determination unit 45 performs a process of determining whether or not the article P is defective. When the X-ray image is newly stored in the X-ray image storage area 413, the quality determination unit 45 acquires this X-ray image and determines whether or not there is an area with luminance lower than the reference value SV. When there is presence of such an area with luminance below the reference value SV in the X-ray image, the quality determination unit 45 determines that the article P corresponding to the X-ray image is a defective product contaminated with foreign matter and sets the defective product determination flag 417. Note that the reference value SV is appropriately set according to the type, for example, of the article P to be inspected.

When a predetermined time has elapsed after setting, the defective product determination flag 417 (more specifically, prior to the start of determining the next article P conveyed after the article P that has been determined as a defective product), the quality determination unit 45 clears the defective product determination flag 417.

(4-6) Sorting Control Unit 46

The sorting control unit 46 executes controls relating to the operation of the arm driving unit 32 in the sorting unit 30. When the light reception signal flag 418 is set in a situation where the defective product determination flag 417 is set (that is, when the article P determined as a defective product is conveyed to the sorting unit 30), the sorting control unit 46 supplies a driving voltage to the arm driving unit 32 to drive the arm 31 at a timing corresponding to the conveying speed (more specifically, the timing at which the article P determined as detective is assumed to have reached the operating range of the arm 31). As a result, the article P determined to be defective is sent to the defective product collection box 95 and excluded from the production line.

(4-7) Abnormal Discharge Determination Unit 47 (Abnormal Discharge Detection Unit)

The abnormal discharge determination unit 47 executes processing for detecting whether or not abnormal discharge occurs in the X-ray irradiator 23. More specifically, with the occurrence of an abnormal discharge, the abnormal discharge determination unit 47 determines if either the first abnormal discharge (abnormal discharge inside the X-ray tube 50) or the second abnormal discharge (abnormal discharge inside the tank 53 outside the X-ray tube 50) is generated (that is, the first abnormal discharge and the second abnormal discharge are individually detected) to thereby specify, based on the determination result, whether the abnormal discharge occurred is abnormal discharge caused by the structure of the X-ray tube 50 or abnormal discharge caused by the lapse of service life.

Specifically, the abnormal discharge determination unit 47 detects occurrence of abnormal discharge when the XOR signal flag 419 or the AND signal flag 420 is set. More specifically, when the XOR signal flag 419 is set (that is, when a change in voltage value (sudden drop) is detected in one of the first electric circuit 59 or the second electric circuit 60), the abnormal discharge determination unit 47 determines that the second abnormal discharge has occurred. That is, the abnormal discharge determination unit 47 detects the second abnormal discharge based on the change in the voltage value in one of the first electric circuit 59 or the second electric circuit 60. Further, when the AND signal flag 420 is set (that is, when a change in voltage value (sudden drop) is detected in both the first electric circuit 59 and the second electric circuit 60), the abnormal discharge determination unit 47 concludes that the first abnormal discharge has occurred. That is, the abnormal discharge determination unit 47 detects the first abnormal discharge based on the change in the voltage value in both the first electric circuit 59 and the second electric circuit 60.

Furthermore, when the abnormal discharge determination unit 47 determines that the second abnormal discharge has occurred (that is, when the XOR signal flag 419 is set), the abnormal discharge determination unit 47 immediately concludes that the generated abnormal discharge is an abnormal discharge caused by the lapse of service life, and sets the maintenance notification flag 421 so as to output notification information (information prompting maintenance such as replacement of the X-ray tube 50 and/or the tank 53) to the administrator.

In contrast, upon determining that the first abnormal discharge has occurred (that is, when the AND signal flag 420 is set), the abnormal discharge determination unit 47 stores the time when the determination has made (that is, the detection time of the first abnormal discharge) in the first abnormal discharge information storage area 415. At this time, the abnormal discharge determination unit 47 acquires information on the previous detection time of the first abnormal discharge stored in the first abnormal discharge information storage area 415. Thereafter, based on the acquired information regarding the detection time, determination is made as to whether the occurrence frequency of the first abnormal discharge is abnormal or not (specifically, whether or not the occurrence number of the first abnormal discharge in a predetermined period P1 is equal to or greater than a first threshold value ΔTh1).

In this determination, when the number of occurrences of the first abnormal discharge in the predetermined period P1 is equal to or greater than the first threshold value ΔTh1 (that is, when the occurrence frequency of the first abnormal discharge is abnormal), the abnormal discharge determination unit 47 concludes that the first abnormal discharge that has occurred is an abnormal discharge caused by the lapse of service life and therefore sets the maintenance notification flag 421 so as to output the notification information to the administrator. When the number of occurrences of the first abnormal discharge is less than the first threshold value ΔTh1 (that is, when the occurrence frequency of the first abnormal discharge is not abnormal), the abnormal discharge determination unit 47 concludes that the generated first abnormal discharge is an abnormal discharge caused by the structure of the X-ray tube 50 and therefore does not set the maintenance notification flag 421.

It is to be noted that depending on the design specification and the operating environment, the predetermined period P1 and the first threshold value ΔTh1 are set with an appropriate value for determining whether or not the occurrence frequency of the first abnormal discharge is large enough to estimate the lapse of the service life of the X-ray tube 50, that, is, for determining whether or not the first abnormal discharge has occurred as an abnormal discharge caused by the lapse of the service life. In the present embodiment, the predetermined period P1 is set to 168 hours (one week) and the first threshold value ΔTh1 is set to 3 (times). It should be noted that the abnormal discharge determination unit 47 is configured to be able to acquire the time in real time.

Here, the above processing by the abnormal discharge determination unit 47 is based on the following principle.

That is, when abnormal discharge occurs, a change (sudden drop) in the voltage value occurs in the circuit (particularly, the first electric circuit 59 and/or the second electric circuit 60) in the X-ray irradiator 23. At this time, when the first abnormal discharge occurs, a change (sudden drop) in the voltage value occurs in both the first electric circuit 59 and the second electric circuit 60. When the second abnormal discharge occurs, a change in voltage value (sudden drop) occurs only in either the first electric circuit 59 or the second electric circuit 60.

The abnormal discharge caused by the structure of the X-ray tube 50 occurs mainly inside the X-ray tube 50, and therefore, in principle, may be generated as the first abnormal discharge. In contrast, because the abnormal discharge due to the lapse of service life occurs inside the X-ray tube 50 and inside the tank 53 outside the X-ray tube 50, the abnormal discharge may be generated as either the first abnormal discharge or the second abnormal discharge.

Accordingly, it is possible to immediately determine that abnormal discharge due to the lapse of service life has occurred when the second abnormal discharge occurs. Therefore, while the XOR signal flag 419 is set, the abnormal discharge determination unit 47 immediately concludes that the abnormal discharge that has occurred is abnormal discharge due to the lapse of the service life and sets the maintenance notification flag 421.

Figure 9:
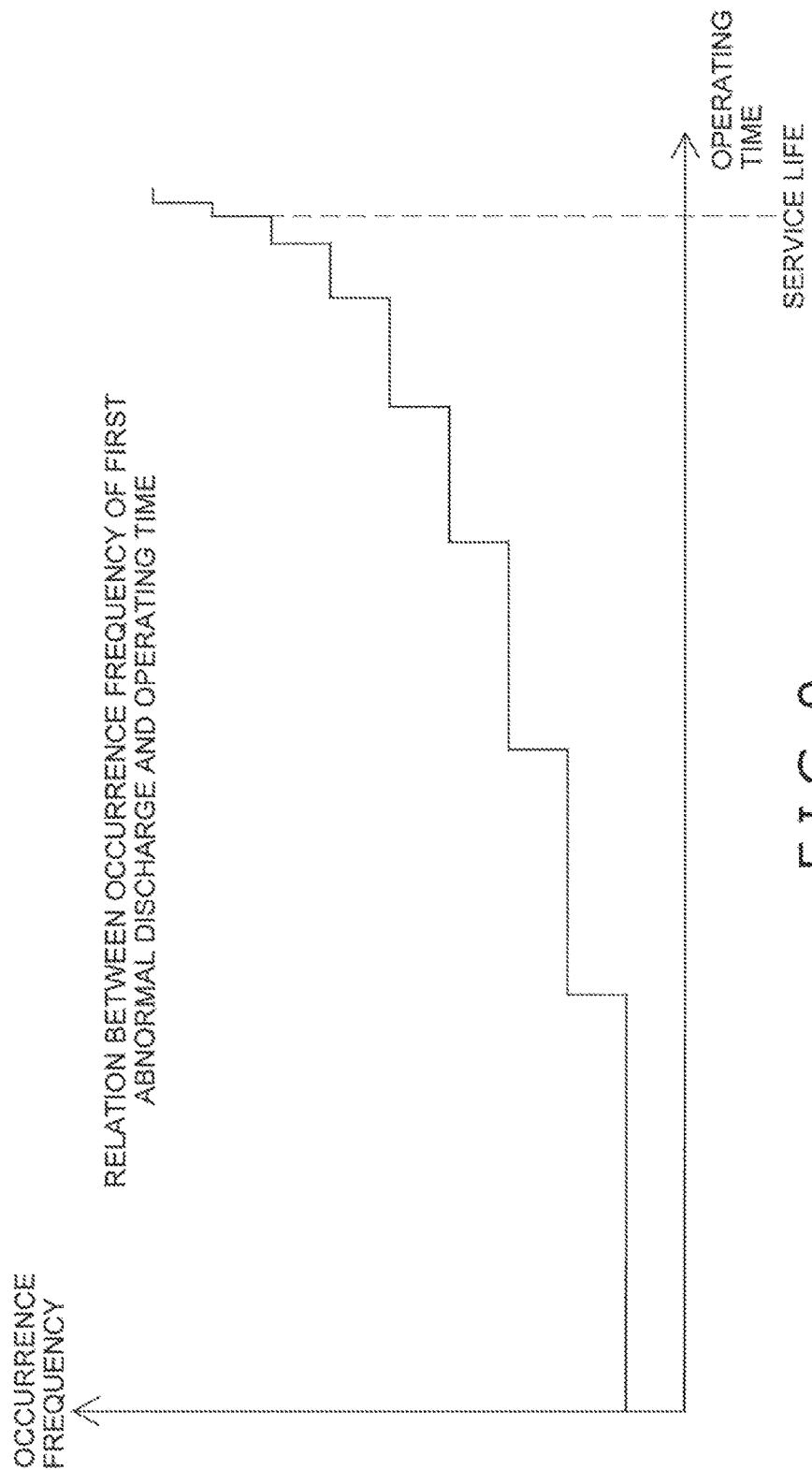
FIG. 9 is a graph showing the relationship between the occurrence frequency of the first abnormal discharge and the operating time.

Furthermore, when the first abnormal discharge occurs, it is necessary to determine whether the generated abnormal discharge corresponds either to abnormal discharge caused by the structure of the X-ray tube 50 or to abnormal discharge due to the lapse of service life. In this regard, as shown in FIG. 9, the frequency at which the first abnormal discharge occurs (that is, the occurrence frequency of the abnormal discharge inside the X-ray tube 50) increases as the number of years the X-ray tube 50 or the tank 53 in use approaches service life (replacement time). It is therefore possible to determine whether or not the first abnormal discharge that has occurred is an abnormal discharge caused by the lapse of the service life on the basis of the occurrence frequency of the first abnormal discharge and determine if maintenance is necessary or not as well.

Accordingly, when the occurrence of the first abnormal discharge is over a predetermined frequency (that is, when the occurrence frequency of the first abnormal discharge is abnormal), it is possible to determine that abnormal discharge due to the lapse of the service life has occurred. Therefore, when the AND signal flag 420 is set, the abnormal discharge determination unit 47 determines whether or not the number of occurrences of the first abnormal discharge in the predetermined period P1 is equal to or greater than the first threshold value ΔTh1. When the number of occurrences of the first abnormal discharge is equal to or greater than the first threshold value ΔTh1, the abnormal discharge determination unit 47 concludes that the first abnormal discharge occurred is an abnormal discharge caused by the lapse of the service life, and sets the maintenance notification flag 421. When the number of occurrences of the first abnormal discharge is less than the first threshold value ΔTh1, the abnormal discharge determination unit 47 concludes that the first abnormal discharge that has occurred is an abnormal discharge caused by the structure of the X-ray tube 50, thus the maintenance notification flag 421 is not set.

Note that after confirming that the XOR signal flag 419 or the AND signal flag 420 is set, the abnormal discharge determination unit 47 clears the XOR signal flag 419 or the AND signal flag 420 which is in the set state.

(4-8) Notification Control Unit 48

When the maintenance notification flag 421 is set, the notification control unit 48 generates notification information (text information and image information such as a warning mark prompting maintenance such as replacement of the X-ray tube 50 and the tank 53 to the administrator), and stores it in the notification information storage area 414. As a result, the generated notification information is outputted to the LCD display 25 by the input/output control unit 42 and displayed on the LCD display 25.

That is, the notification control unit 48 causes the LCD display 25 to output the notification information according to the determination result by the abnormal discharge determination unit 47 (that is, the detection result of the first abnormal discharge or the second abnormal discharge). In other words, when the abnormal discharge determination unit 47 detects the second abnormal discharge, the notification control unit 48 immediately causes the LCD display 25 to output the notification information. When the first abnormal discharge is detected by the abnormal discharge determination unit 47, the notification control unit 48 causes the LCD display 25 not to output the notification information if the number of occurrences of the first abnormal discharge within the predetermined period P1 is less than the first threshold value ΔTh1, and causes the LCD display 25 to output the notification information if the number of occurrences of the first abnormal discharge within the predetermined period P1 is equal to or greater than the first threshold value ΔTh1.

The notification control unit 48 stores the generated notification information in the notification information storage area 414, and then clears the maintenance notification flag 421.

(5) PROCESS FLOW OF CONTROLLER 40

Figure 10:
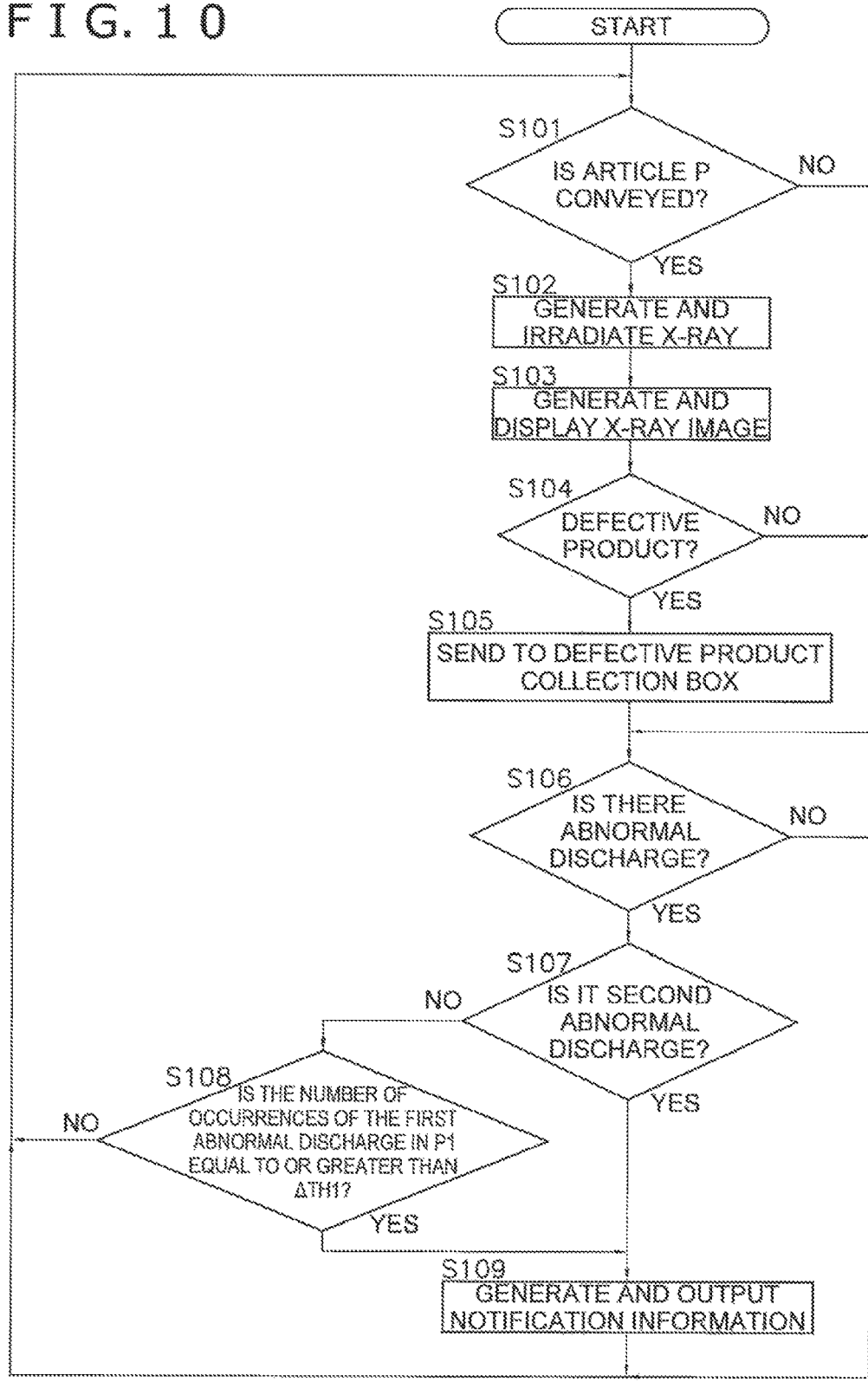
FIG. 10 is a flowchart showing an example of a flow of processing of a controller.

FIG. 10 is a flowchart showing an example of the flow of processing of the controller 40. A processing flow such as the following is executed by the controller 40 when the power supply is turned on. Note that the following flow of process is merely an example and that changing the order of each process, rearranging each process to be in parallel or making changes such as the addition or deletion of a process may be appropriately made according to the design specification and usage environment.

In step S101, the controller 40 determines whether or not an article P is conveyed into the shield box 21 and it is located above the line sensor 24 (the irradiation range Y). When the determination is NO (that is, when the article P is not located above the line sensor 24 (the irradiation range Y)), the process proceeds to step S106. When the determination is YES (that is, when the article P is located above the line sensor 24 (the irradiation range Y)), the process proceeds to step S102.

In step S102, the controller 40 causes the high voltage power supply 51 in the X-ray irradiator 23 to supply a predetermined voltage to the anode electrode 56 and the cathode electrode 57 and causes the filament power supply 52 as well to supply the heating current to the cathode electrode 57, thereby generating X-rays to irradiate the article P. Thereafter, the process proceeds to step S103.

In step S103, the controller 40 generates the X-ray image based on the X-ray fluoroscopic image signal outputted from the line sensor 24 and displays the generated X-ray image on the LCD display 25. Thereafter, the process proceeds to step S104.

In step S104, based on the generated X-ray image, the controller 40 determines if the article P is contaminated with foreign matter, that is, whether or not the article P is defective. If the determination is NO (that is, the article P is not a defective product), the process proceeds to step S106. If the determination is YES (that is, the article P is a defective product), the process proceeds to step S105.

In step S105, the controller 40 supplies a drive voltage to the arm driving unit 32 at a predetermined timing (that is, a timing at which it is assumed that the article P concluded as a defective product has reached the operation range of the arm 31) to drive the arm 31, thereby sending the article P determined to be defective to the defective product collection box 95. Thereafter, the process proceeds to step S106.

In step S106, the controller 40 determines whether or not abnormal discharge is occurring in the X-ray irradiator 23. If such determination is NO (that is, no abnormal discharge has occurred in the X-ray irradiator 23), the process returns to step S101. If the determination is YES (that is, when abnormal discharge occurs in the X-ray irradiator 23), the process proceeds to step S107.

In step S107, the controller 40 determines whether or not the abnormal discharge generated in the X-ray irradiator 23 is the second abnormal discharge (abnormal discharge inside the tank 53 outside the X-ray tube 50). When the determination is NO (that is, when the abnormal discharge occurring in the X-ray irradiator 23 is not the second abnormal discharge but the first abnormal discharge), the process proceeds to step S108. If the determination is YES (that is, when the abnormal discharge occurring in the X-ray irradiator 23 is the second abnormal discharge), the process proceeds to step S109.

In step S108, the controller 40 determines whether or not the occurrence frequency of the first abnormal discharge is large enough to estimate the lapse of the service life of the X-ray tube 50, that is, determines if the occurrence frequency of the first abnormal discharge in the predetermined period P1 is equal to or greater than the first threshold value ΔTh1. When the determination is NO (that is, when the number of occurrences of the first abnormal discharge in the predetermined period P1 is less than the first threshold ΔTh1), the controller 40 concludes that the abnormal discharge that has occurred is an abnormal discharge caused by the structure of the X-ray tube 50, and the process returns to step S101. When the determination is YES (that is, when the number of occurrences of the first abnormal discharge in the predetermined period P1 is equal to or greater than the first threshold ΔTh1), the controller 40 concludes that the abnormal discharge that has occurred is an abnormal discharge caused by the lapse of the service life, and the process proceeds to step S109.

In step S109, the controller 40 generates notification information and causes the LCD display 25 to display the notification information in order to prompt the administrator to maintenance such as replacement of the X-ray tube 50 and/or the tank 53. Thereafter, the process returns to step S101.

(6) CHARACTERISTICS (6-1)

In the inspection sorting apparatus 100, the abnormal discharge determination unit 47 of the controller 40 detects the first abnormal discharge (first discharge) and the second abnormal discharge (second discharge) individually, based on the signal outputted from the abnormal discharge detection circuit 54. In addition, the notification control unit 48 of the controller 40 generates the notification information in accordance with the detection result of the first abnormal discharge or the second abnormal discharge, and displays it on the LCD display 25. As a result, decline in the inspection accuracy of the inspection sorting apparatus 100 is restrained and reliability is excellent.

That is, abnormal discharge (discharge which can be an obstacle to inspection) occurring inside the X-ray tube 50 or inside the tank 53 includes abnormal discharge caused by the lapse of service life and abnormal discharge caused by the structure of the X-ray tube 50. The abnormal discharge caused by the lapse of service life can occur inside the X-ray tube 50 or inside the tank 53 outside the X-ray tube 50 due to deterioration of vacuum degree and deterioration of insulation performance such as insulation oil 61. The abnormal discharge caused by the structure of the X-ray tube 50 occurs inside the X-ray tube 50 due to the fact that the electrons emitted from the cathode electrode 57 stay in the X-ray tube 50 without colliding with the anode electrode 56, thus having little relevance to the lapse of service life.

When abnormal discharge caused by the lapse of service life occurs, using the inspection sorting apparatus in such a state leads to a decline in the inspection accuracy. Therefore, it is desirable to inform the administrator and prompt him to perform maintenance such as replacing the X-ray tube 50 and/or the tank 53.

In this regard, conventionally, when a first abnormal discharge (abnormal discharge inside the X-ray tube 50) occurs, it is detected as an abnormal discharge and notification is given to the administrator, whereas when the second abnormal discharge (abnormal discharge inside the tank 53 outside the X-ray tube 50) occurs, no particular consideration was given to detection and notification. For this reason, when there is no occurrence of abnormal discharge inside the X-ray tube 50, notification was not made to the administrator even when there is an occurrence of the second abnormal discharge (that is, the abnormal discharge due to the lapse of the service life). Therefore, although it is assumed that, notification to the administrator is also not accurately carried out even when the X-ray tube 50 or the like reaches its replacement time, in such case, there is concern that the reliability is poor because the inspection accuracy declines.

In contrast, in the inspection sorting apparatus 100, the controller 40 individually detects the first abnormal discharge and the second abnormal discharge, generates the notification information in accordance with the detection result, and displays it on the LCD display 25. That is, in the inspection sorting apparatus 100, the first abnormal discharge which is abnormal discharge inside the X-ray tube 50, and the second abnormal discharge which is abnormal discharge inside the tank 53 outside the X-ray tube 50 are individually detected and notification is to be carried out according to the detection result. As a result, notification to the administrator can be performed when the second abnormal discharge (that is, an abnormal discharge due to the lapse of service life) occurs, and situations in which notification to the administrator is not accurately performed even when the X-ray tube 50 or the like have reached replacement time is restrained to occur. Therefore, decline in inspection accuracy is restrained and reliability is excellent.

In addition, when abnormal discharge occurs, the inspection sorting apparatus 100 is capable of outputting notification information depending on whether it is the first abnormal discharge or the second abnormal discharge. That is, it is also possible that when the second abnormal discharge occurs, notification is immediately performed whereas when the first discharge occurs, notification is not immediately performed but performed only when the abnormal discharge is specified as abnormal discharge due to the lapse of service life. That is, when abnormal discharge occurs, it is possible to perform notification when the abnormal discharge is due to the lapse of service life and not perform notification when the abnormal discharge is caused by the structure of the X-ray tube 50. Therefore, notifications can be accurately executed only when necessary, and reliability is also excellent with respect to the accuracy of notification.

(6-2)

In the inspection sorting apparatus 100, when the second abnormal discharge is detected, the notification, control unit 48 of the controller 40 causes the LCD display 25 to output the notification information. Consequently, when a second abnormal discharge (that is, an abnormal discharge caused by the lapse of the service life) occurs, notification is immediately performed. As a result, the administrator can be appropriately prompted to perform maintenance such as replacement of the X-ray tube 50 and/or the tank 53, thus the decline in inspection accuracy is restrained.

(6-3)

In the inspection sorting apparatus 100, when the first abnormal discharge is detected, the notification control unit 48 of the controller 40 executes a process so as not to cause the LCD display 25 to display the notification information when the number of occurrences of the first abnormal discharge within the predetermined period P1 is less than the first threshold value ΔTh1, and to cause the LCD display 25 to output the notification information when the number of occurrences of the first abnormal discharge within the predetermined period P1 is equal to or greater than the first threshold value ΔTh1.

Thus, when the first abnormal discharge occurs, notification is performed only when it is specified that the abnormal discharge is due to the lapse of the service life. Therefore, notification is accurately performed only when necessary, and the administrator is appropriately prompted to replace the X-ray tube 50 and/or the tank 53 or the like.

(6-4)

In the inspection sorting apparatus 100, the abnormal discharge determination unit 47 of the controller 40 detects the first abnormal discharge based on the change in the voltage value in both the first electric circuit 59 and the second electric circuit 60, and detects the second abnormal discharge based on the change in the voltage value in one of the first electric circuit 59 or the second electric circuit 60. That is, in the inspection sorting apparatus 100, based on the fact that a change in the voltage value occurs in both the first electric circuit 59 and the second electric circuit 60 when a first abnormal discharge occurs, and a change in the voltage value in either the first electric circuit 59 or the second electric circuit 60 occurs when the second abnormal discharge occurs, when abnormal discharge occurs, the first abnormal discharge and the second abnormal discharge are individually detected in accordance with whether the change in the voltage value, has occurred in one of the first electric circuit 59 or the second electric circuit 60, or that the change in voltage value has occurred in both circuits. As a result, the first abnormal discharge and the second abnormal discharge can be individually detected with high accuracy.

(6-5)

The inspection sorting apparatus 100 includes the X-ray irradiation control unit 43 of the controller 40 for controlling the operation of the X-ray irradiator 23, the line, sensor 24 for detecting X-rays (that is, transmitted X-rays) generated by the X-ray irradiator 23 and transmitted through the article P, and the X-ray image, generation unit 44 of the controller 40 for generating the X-ray image according to the intensity of the transmitted X-rays (the X-ray fluoroscopic image signal) detected by the line sensor 24. That is, the inspection sorting apparatus 100 not only functions as an "X-ray generator" that generates X-rays but also functions as an "X-ray inspection apparatus" that performs a specific inspection based on the result of X-ray irradiation. That means, the inspection sorting apparatus 100, as in the "X-ray inspection apparatus", is capable of appropriately performing notification to the administrator when the X-ray tube 50 or the like reaches its replacement time due to the lapse of the service life of the X-ray irradiator 23, and capable of performing accurate notification only when it is necessary for replacing the X-ray tube 50 and/or the tank 53.

(7) MODIFICATIONS

The inspection sorting apparatus 100 of the above-described embodiment can be appropriately modified as shown in the following modified examples. It should be noted that each modification may be applied in combination with other modifications as long as the modifications do not contradict the present invention.

(7-1) Modification Example A

In the above embodiment, the inspection sorting apparatus 100 includes the sorting unit 30. However, the sorting unit 30 is not always necessary in the inspection sorting apparatus 100, and may be appropriately omitted. For example, a sorting device, for excluding articles P determined to be defective in the inspection sorting apparatus 100 from the production line may be disposed independently instead of the sorting unit 30. Further, the sorting process performed by the sorting unit 30 may be performed manually. That is, the inspection sorting apparatus 100 may be composed of only essential elements to function as an "X-ray generator" for generating X-rays and as an "X-ray inspection apparatus" for performing a specific inspection based on the result of X-ray irradiation.

(7-2) Modification Example B

In the above embodiment, the inspection sorting apparatus 100 functions not only as an "X-ray generator" for generating X-rays but also functions as an "X-ray inspection apparatus" for performing a specific inspection based on the result of X-ray irradiation. However, the inspection sorting apparatus 100 may be configured so as to function only as an "X-ray generator". That is, the inspection sorting apparatus 100 may be configured only by elements necessary for functioning as "X-ray generating apparatus", and the elements necessary for functioning as "X-ray inspection apparatus" may be omitted.

For example, in the above embodiment, the inspection sorting apparatus 100 includes the X-ray irradiation control unit 43, the X-ray image generation unit 44, the quality determination unit 45, and the sorting control unit 46 in the controller 40. However, in the case where the inspection sorting apparatus 100 is configured as an "X-ray generator", any or all of the X-ray irradiation control unit 43, the X-ray image generation unit 44, the quality determination unit 45, and the sorting control unit 46 may be appropriately omitted. In such a case, any or all of the X-ray fluoroscopic image signal storage area 412, the X-ray image storage area 413, the article detection flag 416, the defective product determination flag 417, and the light reception signal flag 418 in the storage unit 41 can also be appropriately omitted.

(7-3) Modification Example C

Figure 11:
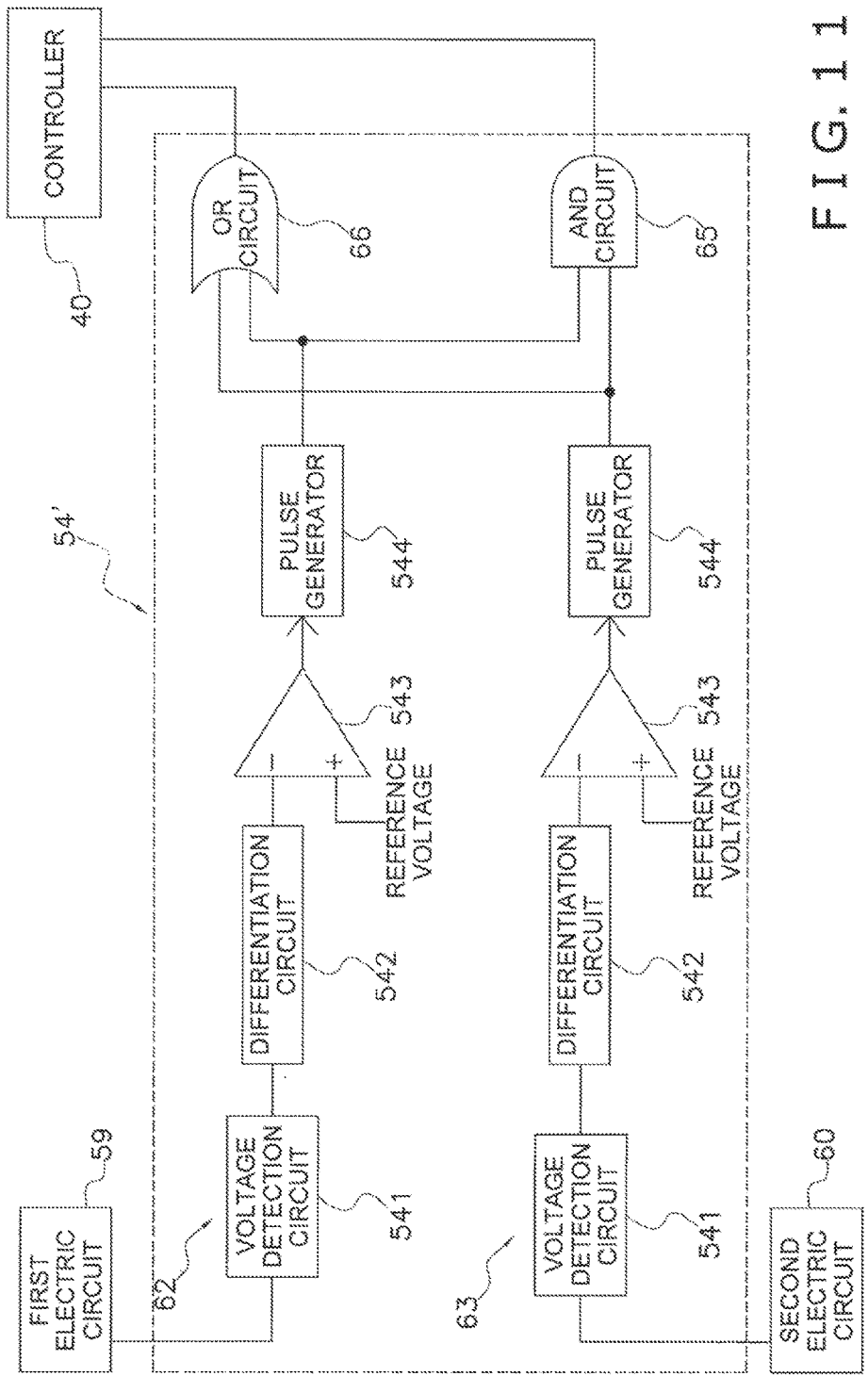
FIG. 11 is a schematic diagram schematically illustrating an abnormal discharge detection circuit according to Modification C.

In the above embodiment, the XOR circuit 64 is disposed in the abnormal discharge detection circuit 54. However, the abnormal discharge detection circuit 54 may be configured, for example, like an abnormal discharge detection circuit 54' shown in FIG. 11. In the abnormal discharge detection circuit 54', an OR circuit 66 is disposed instead of the XOR circuit 64 of the abnormal discharge detection circuit 54.

In the abnormal discharge detection circuit 54', when a pulse is input from any one of the first detection unit 62 and the second detection unit 63 (that is, a when a change in voltage value (sudden drop) occurs in one of or both of the first electric circuit 59 and the second electric circuit 60), the OR circuit 66 outputs a signal (OR signal) to the controller 40.

When such an abnormal discharge detection circuit 54' is employed, effects similar to those of the above embodiment can be obtained by changing the processing of the controller 40 as follows.

That is, a configuration may be adopted in which the input/output control unit 42 sets the OR signal flag (XOR signal flag 419) when the OR signal is input therein so as to allow the XOR signal flag 419 to function as the "OR signal flag" in the storage unit 41. In addition, in a case where the second abnormal discharge occurs, the voltage value in only either of the first electric circuit 59 or the second electric circuit 60 changes (sudden drops). Thus, when the OR signal flag is set while the AND signal flag 420 is not be set, the abnormal discharge determination unit 47 concludes that the second abnormal discharge (abnormal discharge due to the lapse of service life) has occurred, thereby setting the maintenance notification flag 421. A configuration similar to the above embodiment may be adopted for the process of the abnormal discharge determination unit 47 when the AND signal flag 420 is set (that is, when the first abnormal discharge occurs).

Even if the processing of the controller 40 is changed in this manner, when abnormal discharge due to the lapse of service life occurs, the notification information is immediately displayed. Also, when the first abnormal discharge occurs, the notification information is displayed only when necessary (that is, when it is specified as abnormal discharge due to the lapse of service life).

(7-4) Modification Example D

In the above embodiment, the abnormal discharge determination unit 47 of the controller 40 detects the second abnormal discharge based on the change in the voltage value in either of the first electric circuit 59 or the second electric circuit 60, and detects the first abnormal discharge based on the change in the voltage value in both the first electric circuit 59 and the second electric circuit 60. However, the abnormal discharge determination unit 47 of the controller 40 is not limited thereto but may be configured to detect the second abnormal discharge based on the change in the current value in either of the first electric circuit 59 or the second electric circuit 60, and detect the first abnormal discharge based on the change in the current value in both the first electric circuit 59 and the second electric circuit 60.

Figure 12:
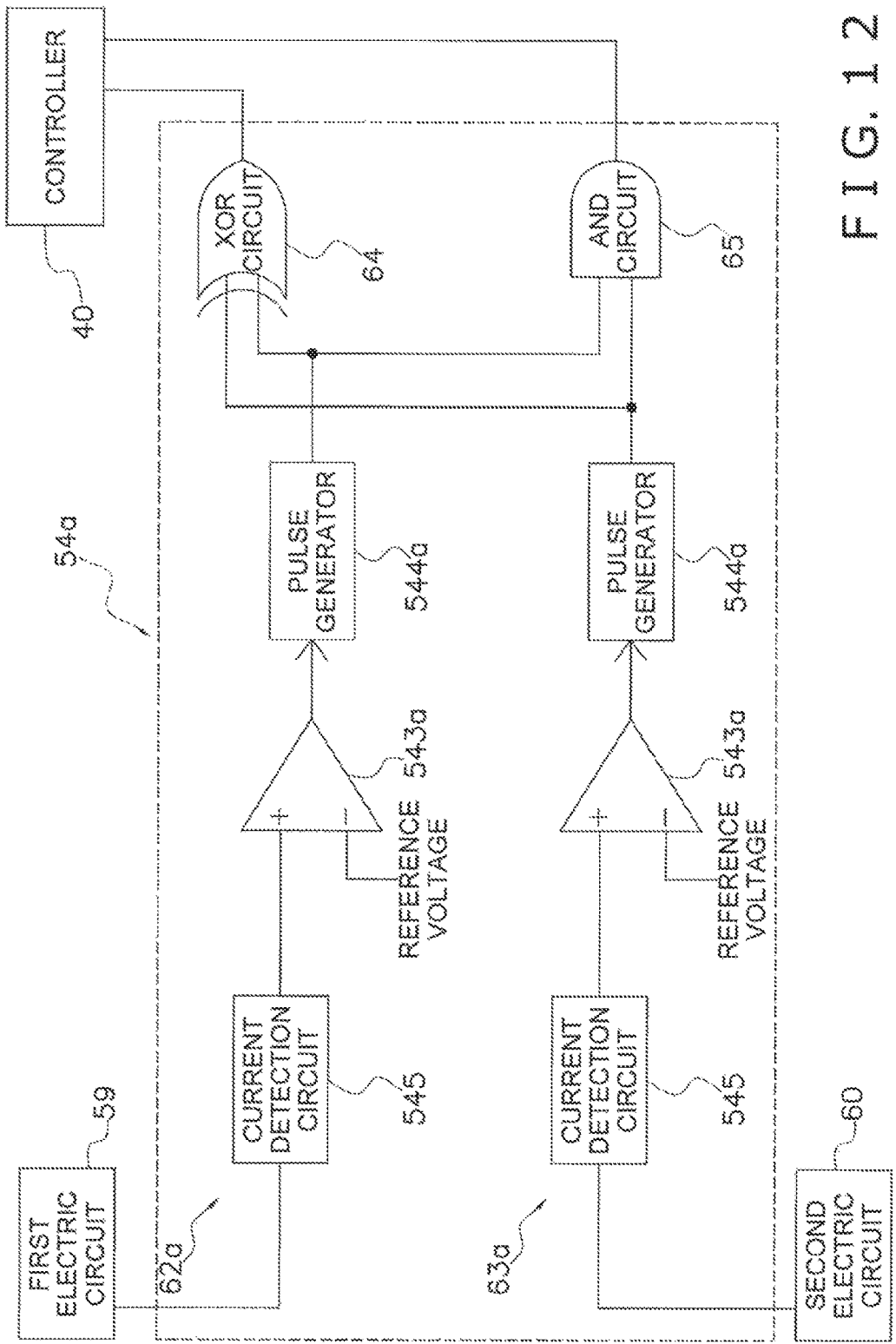
FIG. 12 is a schematic diagram schematically illustrating an abnormal discharge detection circuit according to Modification D.

In such a case, the abnormal discharge detection circuit 54 may be configured, for example, like an abnormal discharge detection circuit 54a shown in FIG. 12. Instead of the first detection unit 62 and the second detection unit 63 of the abnormal discharge detection circuit 54, the abnormal discharge detection circuit 54a includes a first detection unit 62a for outputting pulses in accordance with a change in the current value (sudden rise) in the first electric circuit 59, and a second detection unit 63a for outputting pulses according to a change in the current value (sudden rise) in the second electric circuit 60. Each of the first detection unit 62a and the second detection unit 63a include a current detection circuit 545, a comparator 543a, and a pulse generator 544a connected in series in the order.

The current detection circuit 545 is connected to the first electric circuit 59 or the second electric circuit 60 on the input side. The current detection circuit 545 is connected to the positive input terminal of the comparator 543a on the output side. The comparator 543a is connected to a reference power supply (not shown) at the negative input terminal, and is supplied with a reference current. The comparator 543a is connected to the pulse generator 544a at the output terminal. The pulse generator 544a is connected to the XOR circuit 64 and the AND circuit 65 at the output side.

In the first detection unit 62a and the second detection unit 63a, the current detection circuit 545 detects the value of the current (current value) supplied to the first electric circuit 59 or the second electric circuit 60. The comparator 543a detects a change (sudden rise) in the current value supplied to the first electric circuit 59 or the second electric circuit 60 based on the detection result of the current detection circuit 545. Based on the output of the comparator 543a, the pulse generator 544a outputs a pulse when a change (sudden rise) in the current value supplied to the first electric circuit 59 or the second electric circuit 60 occurs.

Other features of the abnormal discharge detection circuit 54a are substantially the same as those of the abnormal discharge detection circuit 54.

As described above, by configuring the abnormal discharge detection circuit 54a to detect a change (sudden rise) in the current value in the first electric circuit 59 and/or the second electric circuit 60 and output a signal, the same effects as those of the above embodiment can be achieved.

That is, when an abnormal discharge occurs in the X-ray irradiator 23, a change (sudden rise) in the current value in a circuit (particularly the first electric circuit 59 and/or the second electric circuit 60) in the X-ray irradiator 23 will occur. In this case, when the first abnormal discharge occurs, a change (sudden rise) in the current value occurs in both the first electric circuit 59 and the second electric circuit 60. Further, when the second abnormal discharge occurs, a change (sudden rise) in the current value occurs in only one of the first electric circuit 59 and the second electric circuit 60.

Thus, when the second abnormal discharge occurs, the XOR signal flag 419 is set duets the current value change (sudden rise) occurring only in either the first electric circuit 59 or the second electric circuit 60, and notification information is immediately displayed. In addition, when the first abnormal discharge occurs, the AND signal flag 420 is set due to the current value change (sudden rise) occurring in both the first electric circuit 59 and the second electric circuit 60, and notification information is displayed only when necessary on the basis of whether or not the number of occurrences of the first abnormal discharge in the predetermined period P1 is equal to or greater than the first threshold value $\Delta Th1$.

(7-5) Modification Example E

In the above embodiment, when the abnormal discharge determination unit 47 determines that the first abnormal discharge has occurred (that is, when the AND signal flag 420 is set), the abnormal discharge determination unit 47 determines the occurrence frequency of the first abnormal discharge (whether or not the number of occurrences of the first abnormal discharge in the predetermined period P1 is equal to or greater than the first threshold value $\Delta Th1$) based on the detection time of the first abnormal discharge stored in the first abnormal discharge information storage area 415.

However, the abnormal discharge determination, unit 47 may be configured to determine the occurrence frequency of the first abnormal discharge and conclude whether or not to perform notification by another method.

For example, the abnormal discharge determination unit 47 may be configured to being capable of measuring at least a time corresponding to the predetermined period P1, configured to include a register capable of holding information on the number of detections of the first abnormal discharge, and configured to thereby determine the frequency of occurrence of the first abnormal discharge. In this case, the abnormal discharge determination unit 47 may be configured to start time measurement when the occurrence of the first abnormal discharge has been determined (that is, the time at which the first abnormal discharge is detected) and writes the information regarding the detection of the first abnormal discharge in the register as well.

Furthermore, a configuration may be adopted in which when a first abnormal discharge not further detected from the start of the time measurement until the predetermined period P1 elapses, the abnormal discharge determination unit 47 concludes that the number of occurrences of the first abnormal discharge in, the predetermined period P1 is not equal to or greater than the first threshold value $\Delta Th1$, thereby stopping the time measurement and erasing the information held in the register.

In contrast a configuration may be adopted in which when a first abnormal discharge is further detected from the start of time measurement until the predetermined period P1 elapses, the information regarding the first abnormal discharge that is further detected is written in the register. In addition, a configuration may be adopted, in which when the number of detections of the first abnormal discharge in the information held by the register from the start of time measurement until the predetermined period P1 elapses becomes equal to or greater than the first threshold value $\Delta Th1$, the abnormal discharge determination unit 47 concludes that the number of occurrences of the first abnormal discharge in the predetermined period P1 is equal to or greater than the first threshold value $\Delta Th1$ (that is, abnormal discharge due to the lapse of service life has occurred in the first abnormal discharge), and the maintenance notification flag 421 is set.

(7-6) Modification Example F

In the above embodiment, the predetermined period P1 is set to 168 hours (one week), and the first threshold value $\Delta Th1$ is set to 3 (times). However, the predetermined period P1 and/or the first threshold value $\Delta Th1$ can be appropriately changed according to the design specification and the operating environment. For example, the predetermined period P1 may be set to 50 hours or set to 200 hours. Further, for example, the first threshold value $\Delta Th1$ may be set to 2 (times) or may be set to 10 (times).

(7-7) Modification Example G

In the above embodiment, the LCD display 25 functions as the "information output unit" of notification information. However, other components in place of the LCD display 25 may be adopted to function as the "information output unit" for outputting notification information. For example, an LED lamp may be disposed as an "information output unit" at a position visible to the administrator, and by turning on or causing the LED lamp to blink, notification information is outputted to the administrator prompting maintenance such as replacement of the X-ray tube 50 or the tank 53. Also, a speaker may be arranged as the "information output unit" at a position recognizable by the administrator to output a warning sound as notification information to the administrator.

(7-8) Modification Example H

In the above embodiment, the article P determined to be defective is sent to the defective product collection box 95, but no limitation is imposed thereby. A configuration may be adopted in which a defective product transfer conveyor is disposed instead of the defective product collection box 95 so that defective products, are excluded from the production line by sending defective products to the defective product transfer conveyor.

Further, in the above embodiment, the sorting unit 30 excludes the article P determined as defective by the arm 31 from the production line. However, the means for excluding the article P determined to be defective from the production line by the sorting unit 30 is not particularly limited, and may be appropriately selected according to the article P. For example, a configuration may be adopted in which an air injection mechanism instead of the arm 31 is disposed to inject air from the air injection mechanism to the article P determined to be defective, thus excluding the defective products from the production line. In addition, a configuration may be adopted such that, instead of disposing the arm 31, an opening configured to be openable and closable on the conveyor belt 22*d* is formed, and at the timing, when the article P determined as a defective product passes through the opening, the opening is switched from the closed state to the open state, and the defective product is sent to the defective product collection box 95 via the opening.

(7-9) Modification Example I

In the above embodiment, the controller 40 is disposed in the shield box 21. However, the controller 40 does not necessarily have to be disposed in the shield box 21, but may be disposed in another unit or may be disposed independently.

In addition, any or all of the elements (41, 42, 43, 44, 45, 46, 47, and 48) including the controller 40 in the above embodiment are not always necessarily arranged at the same positions (within the same substrate or casing), but may be arranged at a remote location where communication can be established via a communication network.

Also, with respect to any or all of the storage areas (411, 412, 413, 414, and 415) and flags (416, 417, 418, 419, 420, and 421) included in the storage unit 41, the storage areas and flags are not al ways necessarily arranged at the same positions (within the same substrate or casing), but may be arranged at a remote location where communication can be established via a communication network.

In the above-described embodiment, each of the units (42, 43, 44, 45, 46, 47, and 48) included in the controller 40 is configured on the assumption that processing is executed according to the control programs stored in the storage unit 41 (program storage area 411) in order to realize the respective functions. However, the processing relating to any of the units (42, 43, 44, 45, 46, 47, and 48) included in the controller 40 may be configured so as not to be realized by software but realized by hardware.

(7-10) Modification Example J

In the above embodiment, the inspection sorting apparatus 100 inspects foreign matter of the article P and determines whether or not the article P is defective in accordance with the presence or absence of foreign matter. However, the inspection performed by the inspection sorting apparatus 100 is not necessarily limited to the foreign matter inspection of the article P. The inspection sorting apparatus 100 may perform other inspections. For example, the inspection sorting apparatus 100 may be configured to inspect whether or not the weight, the shape, the quantity, or the like of the article P is normal by using a known method based on the generated X-ray image, and determines that the article P whose inspection result is not normal to be defective.

INDUSTRIAL APPLICABILITY

The present invention is available for an X-ray generator and an X-ray inspection apparatus.

The invention claimed is:

1. An X-ray generator including an X-ray tube with an anode electrode and a cathode electrode, and a tank housing the X-ray tube and having insulating oil and/or a solid insulator contained therein, wherein the anode electrode and the cathode electrode are supplied with a predetermined voltage to generate X-ray, the X-ray generator comprising:
an abnormal discharge detection unit configured and arranged to detect individually a first discharge which is an abnormal discharge inside the X-ray tube, and a second discharge which is an abnormal discharge inside the tank outside the X-ray tube;
an information output unit configured and arranged to output a notification information prompting an administrator to replace the X-ray tube or the tank; and
a notification control unit configured and arranged to cause the information output unit to output the notification information in accordance with a detection result by the abnormal discharge detection unit.

2. The X-ray generator according to claim 1, wherein the notification control unit causes the information output unit to output the notification information when the second discharge is detected by the abnormal discharge detection unit.

3. The X-ray generator according to claim 2, wherein when the first discharge is detected by the abnormal discharge detection unit, the notification control unit causes the information output unit not to output the notification information when the number of occurrences of the first discharge within a predetermined period is less than a first threshold value, and to output the notification information when the number of occurrences of the first discharge within the predetermined period is equal to or greater than the first threshold value.

4. The X-ray generator according to claim 2, wherein the abnormal discharge detection unit detects the first discharge based on a change in a value of a current or a voltage in both of a first electric circuit including the anode electrode and a second electric circuit including the cathode electrode, and detects the second discharge based on a change in a value of a current or a voltage in either the first electric circuit or the second electric circuit.

5. The X-ray generator according to claim 1, wherein when the first discharge is detected by the abnormal discharge detection unit, the notification control unit causes the information output unit not to output the notification information when the number of occurrences of the first discharge within a predetermined period is less than a first threshold value, and to output the notification information when the number of occurrences of the first discharge within the predetermined period is equal to or greater than the first threshold value.

6. The X-ray generator according to claim 5, wherein the abnormal discharge detection unit detects the first discharge based on a change in a value of a current or a voltage in both of a first electric circuit including the anode electrode and a second electric circuit including the cathode electrode, and detects the second discharge based on a change in a value of a current or a voltage in either the first electric circuit or the second electric circuit.

7. The X-ray generator according to claim 1, wherein the abnormal discharge detection unit detects the first discharge based on a change in a value of a current or a voltage in both of a first electric circuit including the anode electrode and a second electric circuit including the cathode electrode, and detects the second discharge based on a change in a value of a current or a voltage in either the first electric circuit or the second electric circuit.

8. An X-ray inspection apparatus comprising:
the X-ray generator according to claim 1;
a control unit configured and arranged to control the operation of the X-ray generator;
an X-ray detection unit configured and arranged to detect transmitted X-rays which are X-rays generated by the X-ray generator and transmitted through an inspection target; and
an image generation unit configured and arranged to generate an image in accordance with the transmitted X-rays detected by the X-ray detection unit.

* * * * *